(12) United States Patent
Grauert et al.

(10) Patent No.: US 6,455,538 B1
(45) Date of Patent: Sep. 24, 2002

(54) 1,2,3,4,5,6-HEXAHYDRO-2,6-METHANO-3-BENZAZOCIN-10-OLS

(75) Inventors: Matthias Grauert, Ingelheim; Adrian Carter, Bingen am Rhein; Wolf-Dietrich Bechtel, Appenheim; Thomas Weiser, Nieder-Olm; Rainer Palluk, Bingen am Rhein; Uwe Pschorn, Mainz, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/523,473

(22) Filed: Mar. 10, 2000

Related U.S. Application Data

(63) Continuation of application No. PCT/EP98/05734, filed on Sep. 9, 1998.

(51) Int. Cl.[7] .................... A61K 31/439; A61K 31/485; C07D 221/26; A61P 25/00; A61P 9/00
(52) U.S. Cl. ......................................... 514/295; 546/97
(58) Field of Search ............................ 546/97; 514/295

(56) References Cited

U.S. PATENT DOCUMENTS

| | | | |
|---|---|---|---|
| 4,208,523 A | 6/1980 | Michne et al. | |
| 4,293,556 A | 10/1981 | Merz et al. | |
| 5,607,941 A | * 3/1997 | Merz | 514/289 |
| 5,731,318 A | * 3/1998 | Carter | 514/289 |
| 6,054,604 A | 4/2000 | Grauert et al. | |

FOREIGN PATENT DOCUMENTS

| | | |
|---|---|---|
| CA | 2072814 A | 1/1993 |
| DE | 29 48 308 A1 | 6/1980 |
| DE | 195 28 472 A1 | 2/1997 |
| EP | 0 006 449 A1 | 1/1980 |
| EP | 0 521 422 A1 | 6/1992 |

OTHER PUBLICATIONS

M. Grauert et al; Synthesis and Structure—Activity Relationaships of 6, 7–Benzomorphan Derivatives as Antagonists of the NMDA Receptor—Channel Complex; J. Med Chem. 1997,40 2922–2930.

N. Yuokoyama et al; Synthesis, Analgesic Activity, and Physical Dependence Capacity of 5–Phenyl–6,7–benzomorphan Derivatives; J. Med. Chem. 1979, 22, 537–553.

C.P. Taylor et al; Na+ channels as targets for neuroprotective drugs; Trends in Pharmacological Sciences, 1995, 16, 309–316.

\* cited by examiner

Primary Examiner—Evelyn Mei Huang
(74) Attorney, Agent, or Firm—Robert P. Raymond; Timothy X. Witkowski; Mary-Ellen Devlin

(57) ABSTRACT

Compounds of general formula I

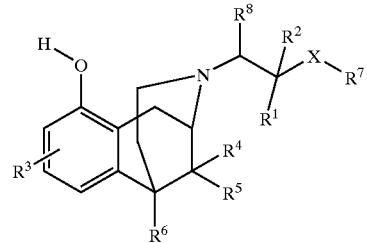

wherein X is a single bond, —O—, $C$–$C_4$-alkylene, or an alkylene bridge having 1 to 8 carbon atoms which may be branched or unbranched and optionally have one or two oxygen atom(s) anywhere in the bridge; $R^1$ is hydrogen, methyl, ethyl, or phenyl; $R^2$ is hydrogen or methyl; $R^3$ is hydrogen, fluorine, chlorine, bromine, hydroxy, methyl, or methoxy; $R^4$ is hydrogen, methyl, or ethyl; $R^5$ is hydrogen, methyl, or ethyl; $R^6$ is hydrogen, methyl, or ethyl; $R^7$ is tert-butyl, cyclohexyl, phenyl optionally substituted by $R^9$ and $R^{10}$, which may be identical or different, or;

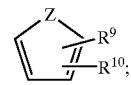

$R^8$ is hydrogen or $C_1$–$C_4$-alkyl; Z is oxygen, NH, or sulfur; $R^9$ is hydrogen, methyl, fluorine, chlorine, bromine, or methoxy; $R^{10}$ is hydrogen, methyl, fluorine, chlorine, bromine, or methoxy; optionally in the form of the individual optical isomers, mixtures of the individual enantiomers or racemates as well as in the form of the free bases or the corresponding acid addition salts with pharmaceutically acceptable acids.

15 Claims, No Drawings

1,2,3,4,5,6-HEXAHYDRO-2,6-METHANO-3-BENZAZOCIN-10-OLS

RELATED APPLICATIONS

This application is a continuation, pursuant to 35 U.S.C. § 365(c), of International Application No. PCT/EP98/05734 filed Sep. 9, 1998.

DESCRIPTION OF THE INVENTION

The present application relates to new substituted 1,2,3,4,5,6-hexahydro-2,6-methano-3-benzazocin-10-ols of general formula I:

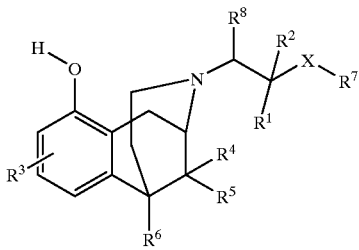

wherein

X denotes a single bond, —O—, $C_1$–$C_4$-alkylene, an alkylene bridge having 1 to 8 carbon atoms which may be branched or unbranched and may have one or two oxygen atom(s) anywhere in the bridge, preferably $C_1$–$C_3$-alkylene—O— or —O—-$CH_2$—$CH_2$—O—, —O—$CH_2$—$CH_2$—NH—;

$R^1$ denotes hydrogen, methyl, ethyl, or phenyl;

$R^2$ denotes hydrogen or methyl;

$R^3$ denotes hydrogen, fluorine, chlorine, bromine, hydroxy, methyl, or methoxy;

$R^4$ denotes hydrogen, methyl, or ethyl;

$R^5$ denotes hydrogen, methyl, or ethyl;

$R^6$ denotes hydrogen, methyl, or ethyl;

$R^7$ denotes tert-butyl, cyclohexyl, phenyl optionally substituted by $R^9$ and $R^{10}$, which may be identical or different,

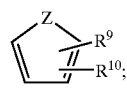

$R^8$ denotes hydrogen or $C_1$–$C_4$-alkyl;

Z denotes oxygen, NH, or sulfur;

$R^9$ denotes hydrogen, methyl, fluorine, chlorine, bromine, or methoxy;

$R^{10}$ denotes hydrogen, methyl, fluorine, chlorine, bromine, or methoxy;

optionally in the form of the individual optical isomers, mixtures of the individual enantiomers or racemates as well as in the form of the free bases or the corresponding acid addition salts with pharmacologically acceptable acids such as, e.g., acid addition salts with hydrohalic acids, for example, hydrochloric or hydrobromic acids, or corresponding organic acids, for example, fumaric or diglycolic acid.

Preferred compounds of general formula I are those wherein, in the above definition $R^4$ and $R^5$ either both simultaneously denote methyl or independently of one another may denote hydrogen or methyl, with at least one of the substituents denoting a methyl group.

Compounds of general formula I are preferred wherein:

X denotes oxygen;

$R^1$ denotes hydrogen, methyl or ethyl;

$R^2$ denotes hydrogen, $R^2$ denotes hydrogen;

$R^4$ denotes hydrogen or methyl;

$R^5$ denotes hydrogen or methyl;

$R^6$ denotes methyl;

$R^7$ denotes phenyl;

$R^8$ denotes hydrogen; and $R^9$ and $R^{10}$ independently of one another denote hydrogen, methyl, fluorine or methoxy, particularly compounds of general formula I wherein, in the above definition, $R^4$ and $R^5$ either both simultaneously denote methyl or independently of one another denote hydrogen or methyl, with at least one of the substituents denoting a methyl group;

The following compounds are most particularly preferred:

(−)-(1R,2″S)-2-(2″-benzyloxy)propyl-4′-hydroxy-5,9,9-trimethyl-6,7-benzomorphan and (−)-(1R,2″S)-2-[2″-(2‴,6‴-difluorobenzyl)oxy]propyl-4′-hydroxy-5,9,9-trimethyl-6,7-benzomorphan in the form of the free bases or the corresponding acid addition salts with pharmacologically acceptable acids.

Unless otherwise stated, the general definitions are used in the following sense:

$C_1$–$C_4$-alkyl or $C_1$–$C_8$-alkyl generally denotes a branched or unbranched hydrocarbon group having 1 to 4 or 1 to 8 carbon atom(s), which may optionally be substituted with one or more halogen atom(s)—preferably fluorine—which may be identical to or different from one another. The following hydrocarbon groups are mentioned by way of example:

methyl, ethyl, propyl, 1-methylethyl (isopropyl), n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2,-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, lower alkyl groups having 1 to 4 carbon atoms, such as methyl, ethyl, propyl, iso-propyl, n-butyl, 1-methylpropyl, 2-methylpropyl or 1,1-dimethylethyl are preferred.

Accordingly, alkylene denotes a branched or unbranched divalent hydrocarbon bridge having 1 to 8 carbon atoms which may optionally be substituted with one or more halogen atom(s)13 preferably fluorine—which may be identical to or different from one another.

Alkoxy generally denotes a straight-chained or branched hydrocarbon group bound via an oxygen atom; a lower alkoxy group having 1 to 4 carbon atom(s) is preferred. The methoxy group is particularly preferred.

Methods of Preparation

The compounds according to the invention may be prepared by methods known from the prior art [WO 97/06146]. The invention relates to the enantiomerically pure compounds as well as the associated racemates.

The key compounds are the nor-benzomorphans 2a to 5a, which are shown in the diagram as the corresponding (−)-enantiomers:

Diagram 1:

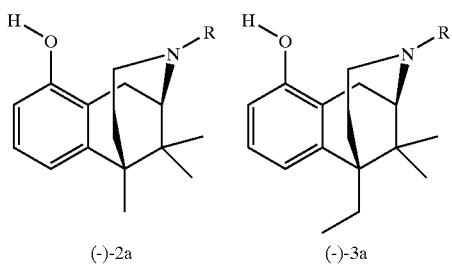

(-)-2a     (-)-3a

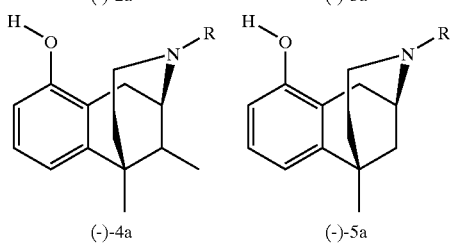

(-)-4a     (-)-5a

R = H

The synthesis of 2 where R=H is described in published German Application No.: 195 28 472.

Compound 3 can be prepared analogously to compound 2. The starting compound is the piperidone 6 which occurs as an intermediate in the synthesis of 2, and which is reacted for example with an ethyltriphenylphosphonium salt instead of with the corresponding ethyl derivative - as is already known from the prior art (cf. Diagram 2).

Diagram 2:

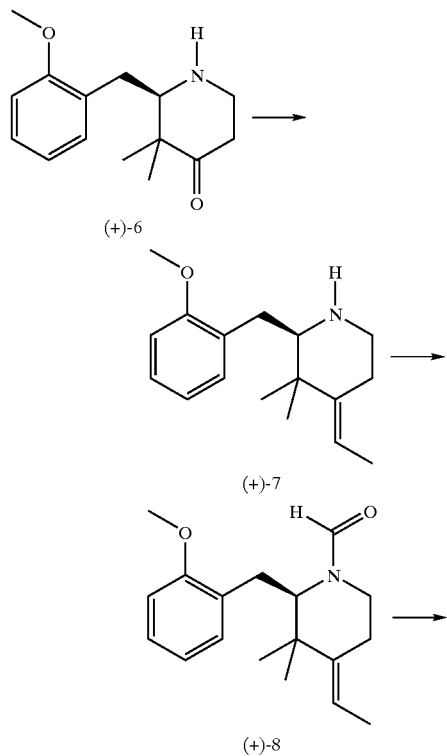

(+)-6

(+)-7

(+)-8

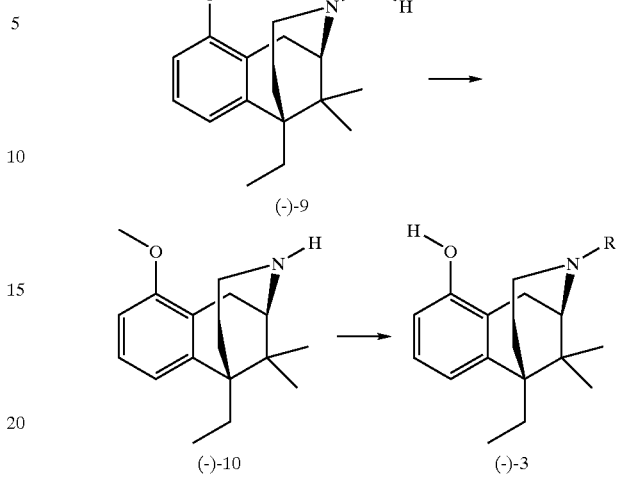

(-)-9

(-)-10     (-)-3

Compound 4 is prepared analogously to the process described in WO 97/06146 from 2-methoxybenzylcyanide 11 and 2-bromopropionic acid 12.

Diagram 3

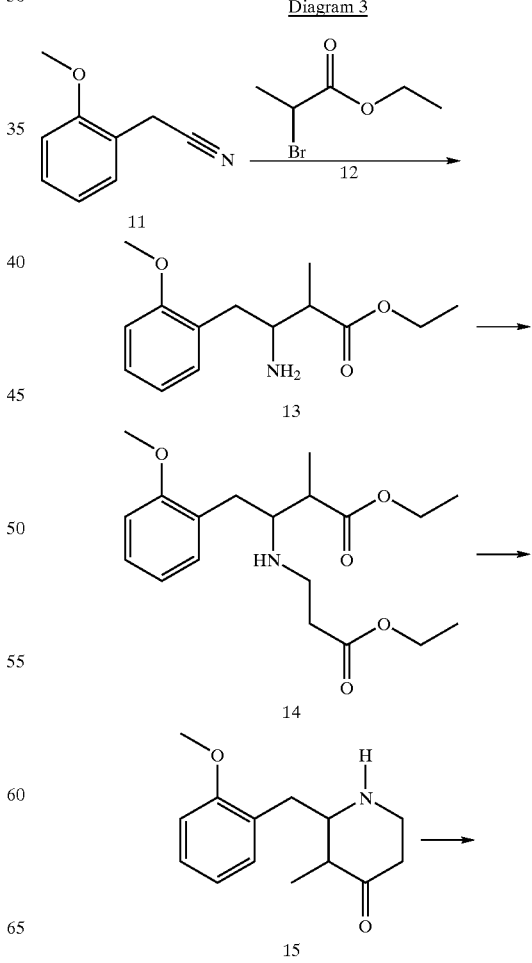

11

13

14

15

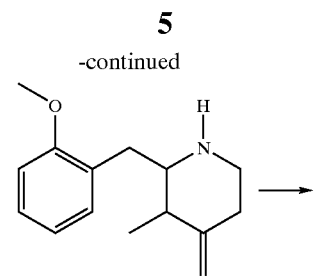

16

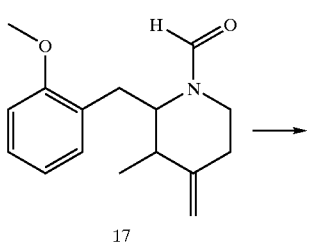

17

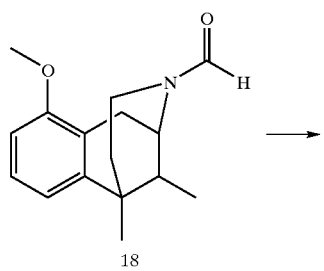

18

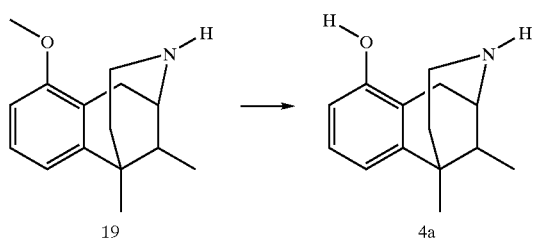

19                           4a

In the first step, for example, 2-methoxybenzylcyanide 11 is reacted with ethyl 2-bromopropionate 12 to obtain the correspondingly substituted 3-amino-2-methylbutanoic acid ester derivative 13 (since in view of the desired end product the alcohol component of the partial ester structure is not important, any other $C_1$–$C_8$-alkyl ester or a benzyl ester may be used):

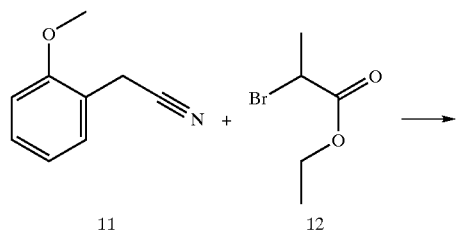

11                    12

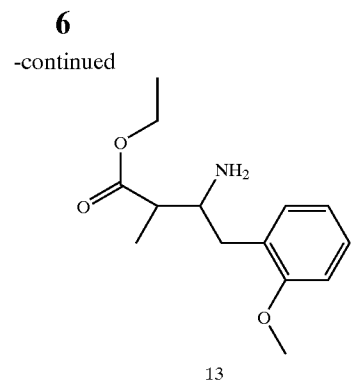

13

In order to carry out this conversion, of the Reformatsky reaction type, an alkylhalosilane, preferably, a trialkylchlorosilane, most preferably trimethylchlorosilane - and zinc powder are placed in a solvent which is inert under the reaction conditions used, preferably an ether, or in a halohydrocarbon, most preferably dichloromethane. After this mixture has been diluted with a polar - inert - solvent, preferably a cyclic ether, most preferably tetrahydrofuran - the reaction mixture is heated - preferably to reflux temperature - and combined with a mixture of the ethyl 2-bromopropionate of general formula 3 with the o-methoxybenzylcyanide and heated further, preferably to reflux temperature. After cooling and filtering off the zinc powder, the reaction mixture is mixed with a reducing agent which is selective regarding the reduction of imino functions - preferably a complex alkali metal borohydride derivative, most preferably sodium cyanoborohydride - and then mixed with an alkanol - preferably a straight-chained or branched $C_1$–$C_4$-alcohol, most preferably ethanol. Then an aqueous solution of a basically reacting compound - preferably ammonia solution, most preferably with concentrated ammonia solution - is added and the organic phase of the reaction mixture is isolated. After drying and evaporation in vacuo, the residue remaining is taken up in an inert solvent - preferably in an aliphatic or aromatic hydrocarbon, most preferably in toluene - and extracted with the aqueous solution of an acid - preferably a mineral acid, most preferably 2 N hydrochloric acid. Finally the aqueous phase is made alkaline with the aqueous solution of a basically reacting compound - preferably ammonia solution, most preferably with concentrated ammonia solution - and then extracted with an organic, water-immiscible extraction agent - preferably with a halohydrocarbon, most preferably with dichloromethane. The extract thus obtained is dried and then concentrated and the 3-amino-2-methylbutanoate derivative of general formula 4 is isolated.

In the second reaction step the ethyl 3-amino-2-methylbutanoate derivative 13 thus obtained is reacted with ethyl acrylate (as, in the light of the desired end product, the alcohol component of the ester structure is not critical, any other $C_1$–$C_8$-alkyl ester or even a benzyl ester may be used here) to obtain the corresponding ethyl 3-(2-ethoxycarbonylethyl)-amino-2-methylbutanoate derivative 14:

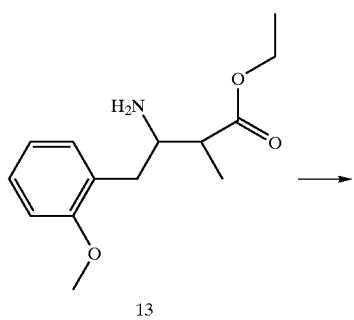

13

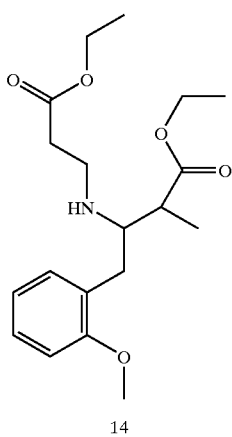

14

In order to carry out this Michael addition reaction the ethyl 3-amino-2-methylbutanoate derivative 13 is dissolved with the ethyl acrylate in a reaction medium which is inert under the reaction conditions - preferably in a straight-chained or branched $C_1$–$C_4$-alkanol, most preferably ethanol - and heated - preferably to reflux temperature. After the reaction has ended the solvent is eliminated in vacuo and the resulting ethyl 3-(2-ethoxycarbonylethyl)amino-2-methylbutanoate derivative 14 is isolated.

In the subsequent third step of the reaction the 3-(2-ethoxycarbonylethyl)amino-2-methylbutanoate derivative 14 resulting from the preceding step of the reaction is cyclized to form the corresponding piperidone derivative 15:

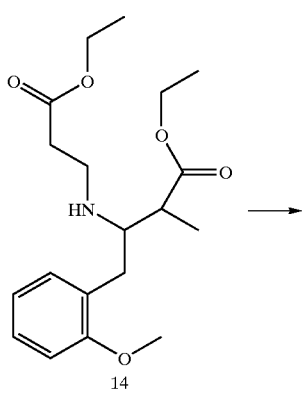

14

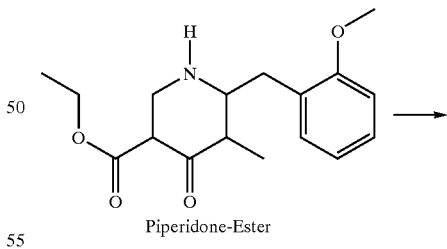

Piperidone-Ester

In order to carry out the Dieckmann's ester condensation type cyclization step, the 3-(2-ethoxycarbonylethyl)amino-2-methylbutanoate derivative 14 is dissolved in a solvent which is inert under the cyclization conditions - preferably in an aliphatic or aromatic hydrocarbon, most preferably in toluene - and heated to reflux temperature in the presence of a basically reacting compound, preferably an alkali metal alkoxide of a branched or unbranched $C_1$–$C_4$-alcohol, most preferably potassium-tert-butoxide, and the components of the reaction mixture which are volatile at these temperatures are eliminated by distillation - for example by azeotropic reaction. After the reaction has ended, the reaction mixture is hydrolyzed and mixed with the aqueous solution of an acidically reacting compound - preferably with aqueous inorganic acids, most preferably with concentrated hydrochloric acid. Then a water-immiscible extraction agent which is inert under these conditions, - preferably a dialkylether, most preferably diethylether - is added and mixed with the aqueous solution of a basically reacting compound, preferably with aqueous ammonia solution, most preferably with concentrated ammonia solution. After separation of the organic phase as well as exhaustive extraction of the aqueous phase the combined organic extracts are washed with water, dried and evaporated down in vacuo and the resulting piperidone ester is isolated.

Alternatively the Dieckmann condensation described above can also be carried out by means of titanium tetrachloride in a halogenated hydrocarbon - preferably dichloromethane [M. N. Deshmukh et al., Synth. Commun. 25 (1995) 177].

In the fourth step of the reaction the piperidone derivative (piperidone ester) thus obtained is saponified and decarboxylated under alkaline or acid conditions to form the corresponding 3-methyl-4-piperidone derivative.

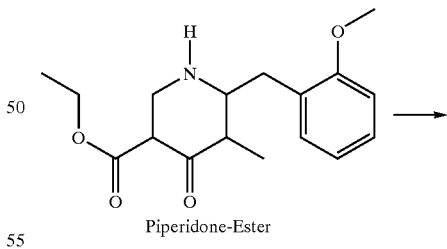

Piperidone-Ester

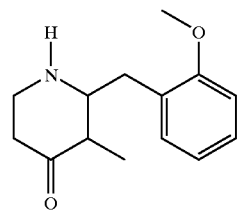

15

For this the piperidone ester is heated, preferably to reflux temperature, in a polar, aqueous solvent or solvent mixture

- preferably in a mixture of a straight-chained or branched $C_1$–$C_4$-alkanol and water, most preferably in an ethanol/water mixture - with a basically or acidically reacting compound - preferably with an alkali metal hydroxide or an inorganic acid, most preferably with sodium hydroxide or if an acid is used, for example, in the presence of hydrochloric acid or sulfuric acid. After saponification has been completed the reaction medium is eliminated in vacuo and the residue is taken up in a solvent suitable for the subsequent salt formation - preferably a polar organic solvent, most preferably in acetone - and the corresponding acid addition salt is precipitated.

The subsequent Wittig reaction with methyltriphenylphosphonium bromide leads in the next step to the corresponding 4-methylene-piperidine derivative 16, which can be isolated in the form of its acid addition salt - preferably in the form of a hydrohalide, most preferably in the form of its hydrochloride.

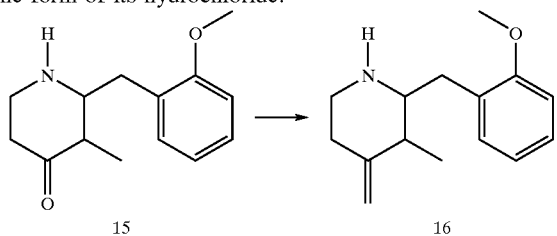

15                   16

In order to carry out the Wittig reaction the 3-methylpiperidone derivative 15 in the form of its acid addition salt - for example as the hydrochloride - is dissolved in water and combined with a basically reacting compound or - preferably - the aqueous solution thereof, most preferably, concentrated aqueous ammonia solution is used.

The aqueous phase is extracted with an organic, water-immiscible solvent - preferably with a haloalkane, most preferably with dichloromethane. After drying and evaporation in vacuo the residue is taken up in a reaction medium which is inert under the conditions used for the Wittig reaction - preferably in a cyclic ether, most preferably in tetrahydrofuran - and combined with a Wittig reagent which generates a methylene group - preferably a methyltriphenylphosphonium halide, most preferably with methyltriphenylphosphonium bromide - in the presence of a basically reacting compound, preferably an alkali metal alkoxide, most preferably potassium tert-butoxide and - depending on the reactivity of the particular educts used - reacted at a temperature in the range from 0 to 80° C. - preferably in a range from 20 to 60° C. and most preferably at about 40° C. After the reaction has ended the reaction mixture is combined with water and a water-immiscible organic solvent - preferably with a haloalkane, most preferably dichloromethane - and the organic phase is separated off. After exhaustive extraction of the aqueous phase and drying of the combined extracts, the extraction agent is eliminated, the residue is dissolved in a solvent suitable for the formation of an acid addition salt, preferably in a branched or unbranched $C_1$–$C_4$-alkanol, most preferably in isopropanol, and combined with a suitable acid, preferably an inorganic acid - such as, for example, a hydrohalic acid, most preferably with concentrated hydrochloric acid - and the acid addition salt of the Wittig product 16 which crystallizes out is isolated.

In the subsequent reaction step the piperidine nitrogen is formylated - for example, with n-butylformate - yielding the corresponding N-formyl-3-methyl-4-methylene-piperidine derivative:

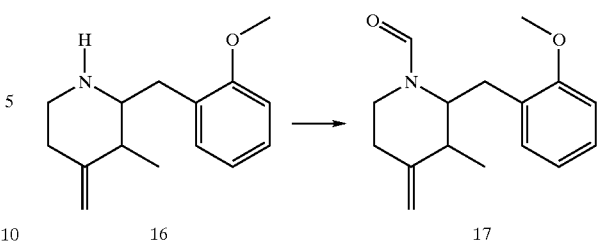

16                   17

To do this the piperidine derivative of type 16, which can be isolated in the preceding step as for example, a hydrohalide, is first converted into the corresponding free base, for example by dissolving the piperidine derivative in water and combining it with a basically reacting compound - preferably with the aqueous solution of a basically reacting compound and most preferably with concentrated ammonia solution, and extracting the free piperidine with a organic solvent, preferably with a halogenated hydrocarbon and most preferably with dichloromethane. After the extract has been dried and the extraction agent has been distilled off the free base is taken up in an organic solvent - such as, for example, a hydrocarbon, preferably in an alkyl-aromatic compound, most preferably in toluene - and reacted with a formylating agent - preferably with an alkylformate, most preferably with n-butylformate - and the reaction product 17 is isolated.

In the subsequent cyclization reaction, in the eighth step of the process, the benzomorphan structure of type 18 is finally synthesized in the presence of correspondingly reactive Lewis acids - such as, for example, inorganic salt acids, particularly hydrobromic acid and preferably with sulfonic acids or with aluminium(III) halides, such as, e.g., aluminium trichloride.

The following reaction step results in the cleaving of the formyl group and thus produces the corresponding 4'-methoxy-5,9-dimethyl-6,7-benzomorphan 19.

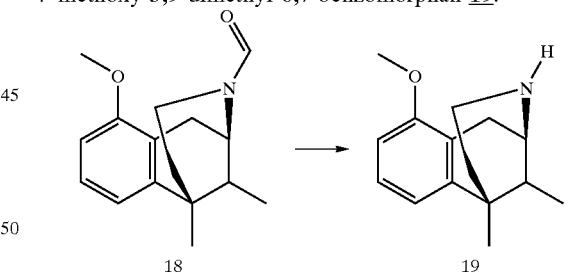

18                   19

To do this the formylbenzomorphan 18 is dissolved in a polar solvent - preferably in an alkanol, most preferably in n-propanol - and combined with an acidically reacting compound - preferably with the aqueous solution of an inorganic acid, most preferably with concentrated hydrochloric acid - and then heated. After cleaving the formyl group, the reaction mixture is evaporated down, combined with water and extracted with a water-immiscible solvent - preferably with an ester of a carboxylic acid, most preferably ethyl acetate. The aqueous phase thus purified is made basic, preferably with concentrated ammonia solution, and extracted with an organic solvent - preferably with a halohydrocarbon, most preferably with dichloromethane. After drying and concentration by evaporation of the com bined organic extracts, the corresponding (−)-4'-methoxy-5, 9-dimethyl-6,7-benzomorphan 19 may be isolated, for example.

In this step, if this has not already been done, the stereoisomers which are still present as a mixture can be separated. The isolation may be effected using the methods described above or by methods known in the art for separating optical isomers.

In the following step the (−)-4'-methoxy-5,9-dimethyl-6, 7-benzomorphan 19 thus obtained may be subjected to ether splitting under acidic conditions - preferably with an inorganic acid, e.g., with hydrohalic acid and most preferably with hydrobromic acid - resulting in the corresponding free partial phenol structure.

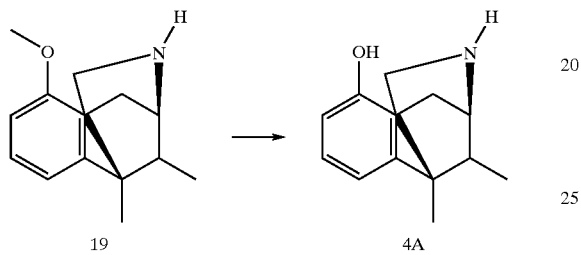

The ether cleavage is carried out under acidic conditions; it has proved beneficial to use inorganic acids. The use of hydrobromic acid has proved particularly advantageous. The saponification product resulting from this saponification can be obtained in this way, for example, in the form of its hydrobromide.

Compound 5 is prepared by the reaction sequence shown in Diagram 4.

Diagram 4:

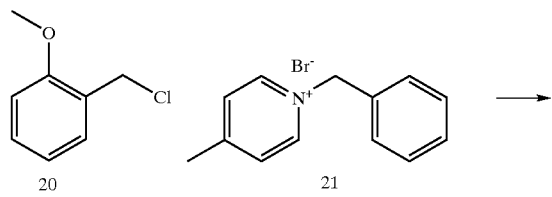

Diagram 5:

The N-substituent is introduced by reacting the key compounds 2a to 5a with acylating agents to obtain the intermediate compounds 25 and subsequently reducing them or by directly alkylating the key compounds 2a to 5a with alkylating agents or by reacting with aldehydes to obtain 26 and subsequent reduction. Diagram 5 shows these methods for the key compound (−)-2a a by way of example.

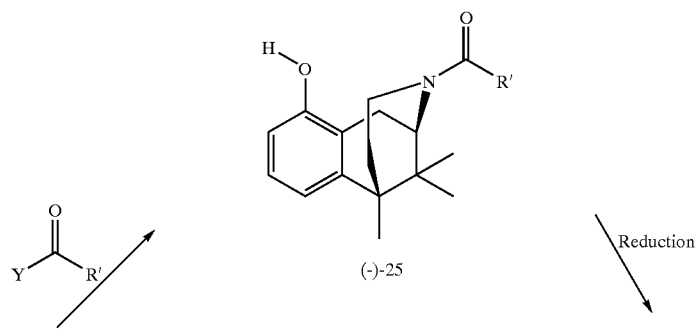

-continued

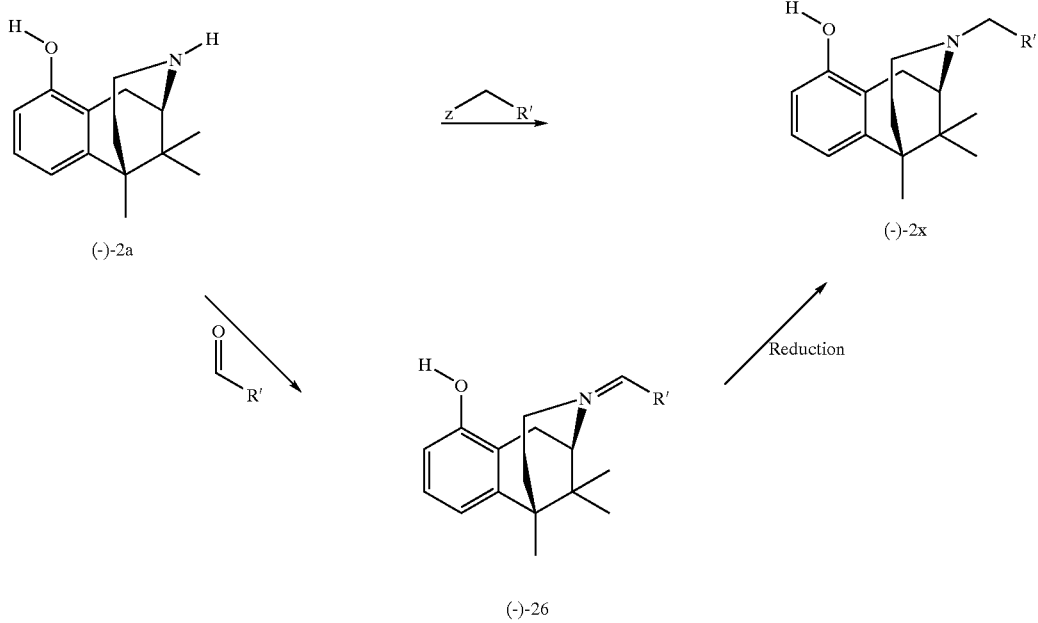

The compounds according to the invention can be synthesized by regioselectively substituting the aromatic benzomorphan species - using the methods known per se from the prior art. An example of the introduction of a substituent $R^3$ according to general formula I is given for compound (−)-2b b in Diagram 6.

Diagram 6:

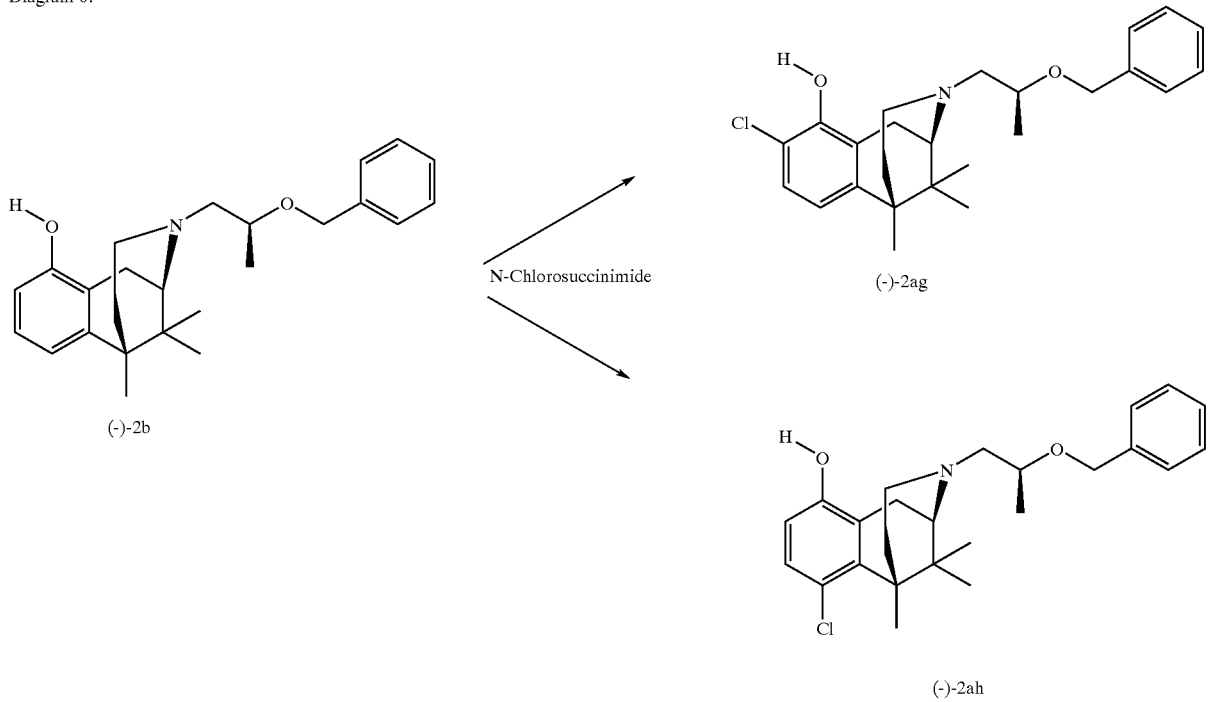

Biological Properties

It has been found that cell damage and loss of function occurring as a result of hypoglycemia, hypoxia, anoxia and ischemia are due to increased synaptic activity to some extent. A series of experiments have demonstrated that hypoglycemic and hypoxic conditions of this kind lead to massive depolarization of the affected cells. This depolarization in turn causes a pathogenic rise in intracellular calcium and additionally causes an increased release of excitatory amino acids in the neuronal tissue. The voltage-dependent sodium channel has a key role in this cascade.

Thus, blocking it can prevent the depolarization of the cells, thereby reducing the calcium influx through voltage-dependent calcium channels and in the neuronal tissue through NMDA-receptor channels. Furthermore, the reduced influx of sodium ions into the cell prevents the calcium/sodium exchanger from operating in the other direction and carrying calcium into the cell. In neuronal tissue the reduced influx of sodium ions into the cell also prevents the glutamate transporter from operating in the other direction and releasing glutamates [C. P. Taylor and B. S. Meldrum, TIPS 16 (1995) 309; J. Urenjak and T. P. Obrenovitch, Am. Soc. Phar. Exp. Ther. 48 (1996) 21].

Surprisingly, it has now been found that the compounds according to the invention of general formula I, unlike the compounds known from the prior art [EP-B-0 521422], have no appreciable affinities for the NMDA-receptor ($K_i$ [$^3$H] MK801: >10000 nM). On the contrary, it was found rather that the compounds according to the invention are blockers of the voltage-dependent sodium channel. These are compounds which competitively or non-competitively displace batrachotoxin (BTX) with a high affinity from the binding site on the sodium channel. Such substances exhibit "use-dependency" when the sodium channels are blocked, i.e., for binding the substances at the sodium channel, first of all the sodium channels have to be activated. Maximum blockage of the sodium channels is only achieved after repeated stimulation of the sodium channels. Consequently, the substances preferably bind to sodium channels which are multiply activated. As a result the substances are capable of activity preferentially in those regions of the body which are pathologically overstimulated.

BTX-binding to the sodium channel serves as a test system for detecting the sodium channel-blocking effect [S. W. Postma & W. A. Catteral, Mol. Pharmacol. 25, 219–224 (1984)], as do patch-clamp experiments which show that the compounds according to the invention block the electrically stimulated sodium channel in a "use-dependent" manner [W. A. Catteral, Trends Pharmacol. Sci., 8, 57–65 (1987)].

Moreover, the compounds according to the invention are shown to have a neuroprotective effect by the blockade of veratridin-induced glutamate release [S. Villauneva, P. Frenz, Y. Dragnic, F. Orrego, Brain Res. 461, 377–380 (1988)]. Veratridine is a toxin which permanently opens up the sodium channel. This leads to an increased influx of sodium ions into the cell. By means of the cascade described above, this increased influx of sodium leads to an increased release of glutamate in the neuronal tissue. This increased release of glutamate can be antagonized with the compounds according to the invention.

Anticonvulsant properties of the substances according to the invention were demonstrated by their protective effect against spasms caused by the maximum electric shock in mice [M. A. Rogawski & R. J. Porter, Pharmacol Rev. 42, 223–286 (1990)] - neuroprotective properties were demonstrated by a protective effect in a rat-MCAO model [U. Pschorn & A. J. Carter, J Stroke, Cerebrovascular Diseases, 6, 93–99 (1996)].

There are also descriptions of sodium channel blockers being used to treat cyclophrenia (manic depressive disorder) [J. A. Calabrese, C. Bowden, M. J. Woyshville in: Psychopharmacology: The Fourth Generation of Progress (Eds.: D. E. Bloom & J. Kupfer) 1099–1111, Raven Press Ltd. New York]. These results demonstrate that the 1,2,3,4,5,6-hexahydro-2,6-methano-3-benzazocin-10-ols of general formula I can be used for treating diseases caused by dysfunction due to overstimulation. These include diseases such as arrhythmia, spasms, cardiac and cerebral ischemia as well as neurodegenerative disorders of various origins. For example, the following may be mentioned: epilepsy, hypoglycemia, hypoxia, anoxia, brain trauma, cerebral edema, cerebral stroke, perinatal asphyxia, amylotropic lateral sclerosis, Huntington's disease, Alzheimer's disease, Parkinson's disease, cyclophrenia, hypotonia, cardiac infarct, cardiac rhythm disorders, angina pectoris, pain, anesthesia and local anesthesia.

The following compounds have proved particularly effective in this context:

(−)-(1R,2″S)-2-(2″-benzyloxy)propyl-4′-hydroxy-5,9,9-trimethyl-6,7-benzomorphan and (−)-(1R,2″S)-2-[2″-(2‴,6‴-difluorobenzyl)oxy]-propyl-4′-hydroxy-5,9,9-trimethyl-6,7-benzomorphan.

The compounds according to the invention can be prepared from compounds known in the art, using the processes described in the following Examples, inter alia.

In particular the present invention relates inter alia to the following method of preparing norbenzomorphans of general formula 5, characterized in that a) o-methoxychlorbenzylchloride 20 is reacted with the benzylpyridinium bromide 21 to obtain tetrahydropyridine 22

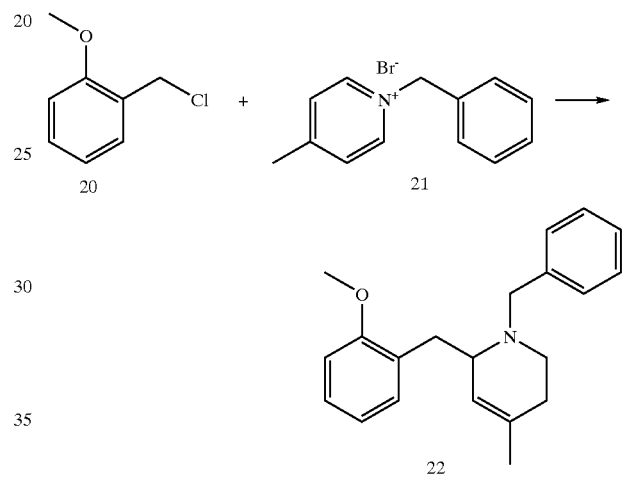

and b) the tetrahydropyridine derivative 22 is rearranged to obtain the N-benzylbenzomorphan derivative 23

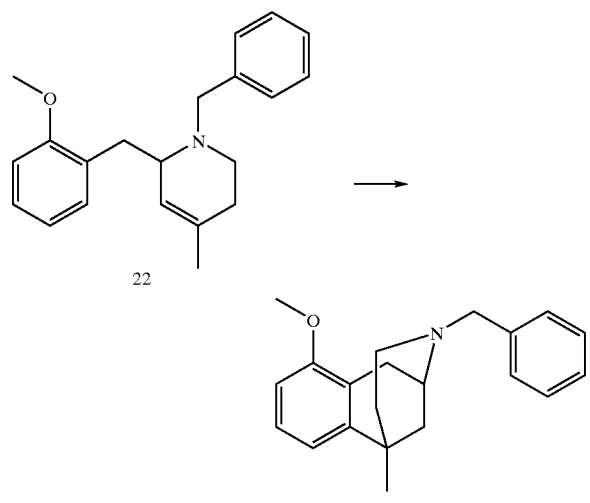

and c) the amino nitrogen is debenzylated to obtain the methoxybenzomorphan derivative 24

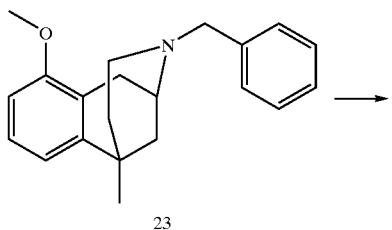

23

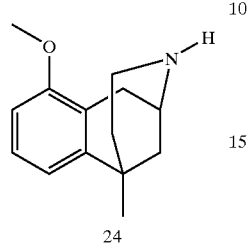

24 and d) the phenolether 24 and the benzomorphan derivative 5 are isolated

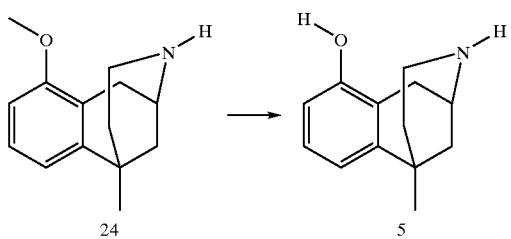

24     5

In addition, the present invention relates to a process for preparing norbenzomorphans of general formula I

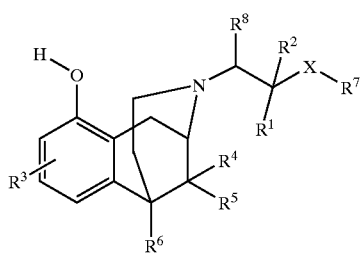

I wherein a) a benzylcyanide of general formula 32 wherein $R_{30}$ denotes a $C_1$–$C_4$-alkyl group, is subjected to the conditions of a Reformatsky reaction with a halocarboxylate of general formula 33, wherein $R_{40}$ denotes $C_1$–$C_8$-alkyl or benzyl, in the presence of an alkylhalosilane - preferably a trialkylchlorosilane and most preferably trimethylchlorosilane - and zinc powder in an inert solvent - preferably in an ether or in a halohydrocarbon and most preferably with dichloromethane and in the presence of a reducing agent which is selective with regard to the reduction of imino functions - preferably in the presence of an alkali metal borohydride derivative and most preferably in the presence of sodium cyanoborohydride - and the resulting carboxylic acid ester derivative of general formula 34 is isolated

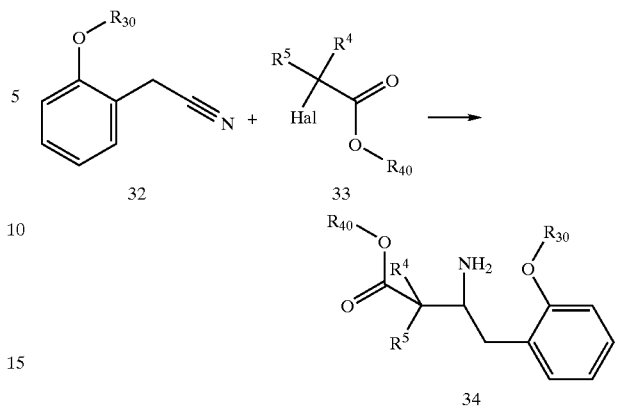

and b) the carboxylic acid ester derivative of general formula 34 is subjected to the conditions of a Michael addition reaction with an acrylic acid ester, wherein the alcohol component $R_{50}$ denotes a $C_1$–$C_8$-alkyl group or a benzyl group, in a solvent which is inert under the reaction conditions selected - preferably in an alkanol and most preferably in ethanol - and the resulting Michael addition product of general formula 35 is isolated

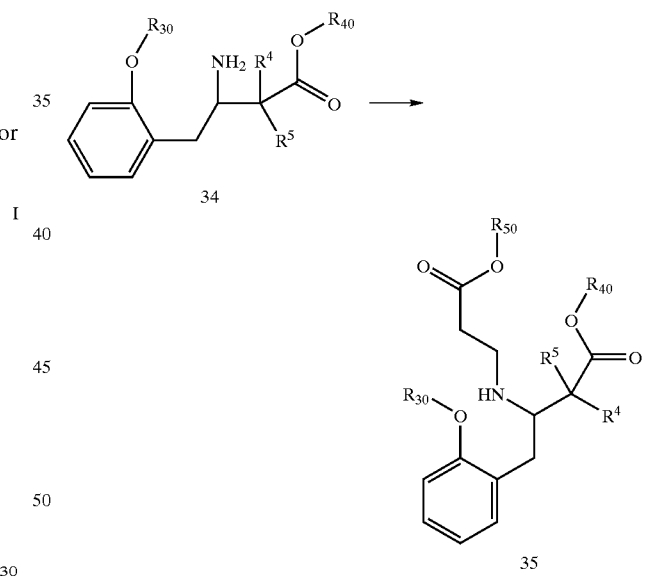

and c) the carboxylic acid diester derivative of general formula 35 thus prepared is subjected to the conditions of Dieckmann's ester condensation in an inert solvent - preferably in an aliphatic or aromatic hydrocarbon and most preferably in toluene - in the presence of a basically reacting compound - preferably in the presence of an alkali metal alkoxide, a branched or unbranched $C_1$–$C_4$-alkanol and most preferably in the presence of potassium-tert-butoxide - and the resulting piperidone derivative of general formula 36 is isolated

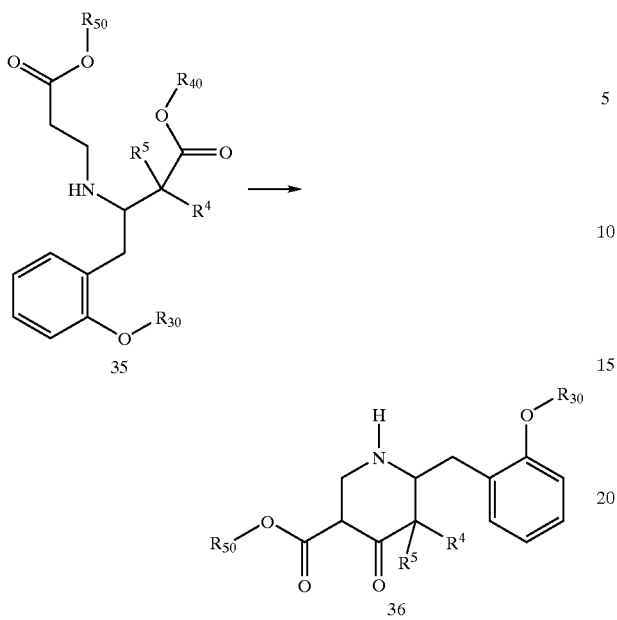

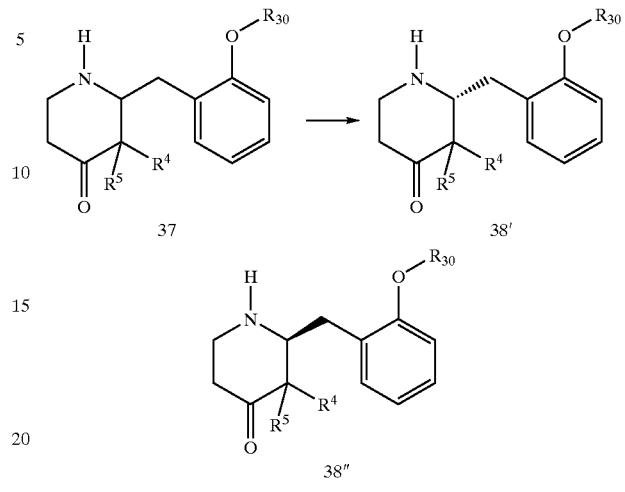

and d) the piperidone derivative 36 is saponified and decarboxylated under acid or alkaline conditions, preferably in the presence of an alkali metal hydroxide or an inorganic acid and most preferably in the presence of sodium hydroxide, in a polar solvent or solvent mixture, preferably in a mixture of a straight-chained or branched $C_1$–$C_4$ alkanol and water and most preferably in an ethanol/water mixture, with heating, to obtain the corresponding piperidone ester derivative of general formula 37 which is isolated, and optionally the corresponding acid addition salt is prepared with an acid and isolated

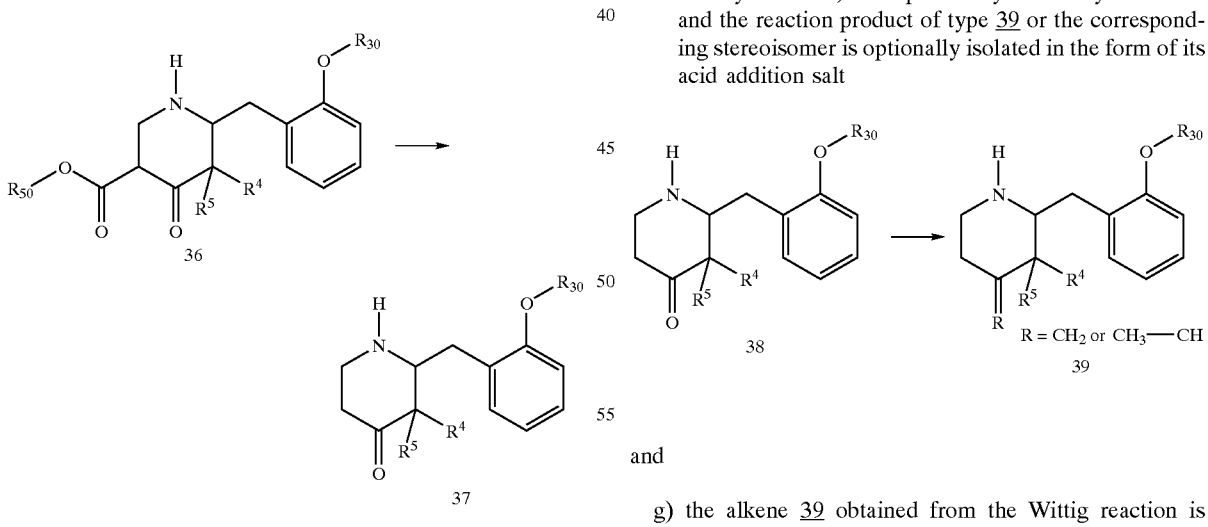

and e) if desired, the mixture of stereoisomers thus obtained is dissolved in a reaction medium which is inert with regard to the enantiomer separation, optionally after the release of the enantiomeric free bases, combined with a suitable stereoisomer of an organic acid suitable for salt formation with a stereoisomer of the enantiomer mixture, the desired stereoisomer is isolated in the form of its addition salt with the optically active acid f) the pure stereoisomer 38' or 38" or the isomer mixture 38 thus obtained is subjected to a Wittig reaction after liberation from the enantiomerically pure acid addition salt in an inert solvent with a Wittig reagent generating a $CH_2$= or $CH_3$—CH= grouping, preferably with an ethyltriphenylphosphonium halide or with a methyltriphenylphosphonium halide, most preferably with methyltriphenylphosphonium bromide or ethyltriphenylphosphonium bromide in the presence of a basically reacting compound - preferably in the presence of an alkali metal alkoxide, most preferably potassium tert-butoxide - in an inert reaction medium - preferably in a cyclic ether, most preferably in tetrahydrofuran - and the reaction product of type 39 or the corresponding stereoisomer is optionally isolated in the form of its acid addition salt and g) the alkene 39 obtained from the Wittig reaction is optionally first liberated from the acid addition salt thereof and the free base of type 39 is dissolved in an organic solvent - preferably in a halogenated hydrocarbon and most preferably in dichloromethane - and subjected to a formylation reaction at the piperidine nitrogen with a formylating agent - preferably n-butylformate - and the reaction product of type 40 or the corresponding stereoisomer is isolated

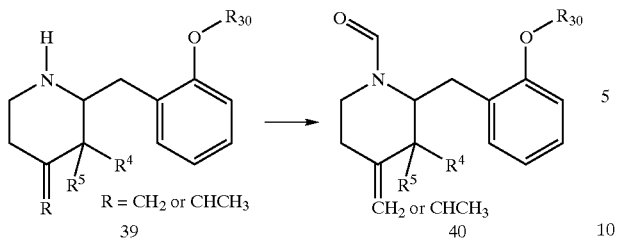
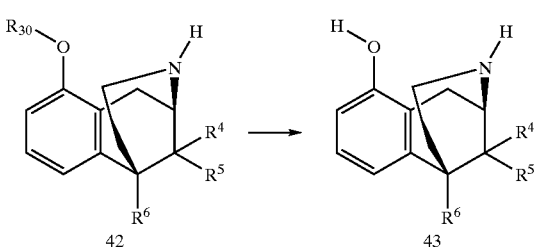

and h) the formyl compound 40 thus obtained - or the corresponding stereoisomer - is reacted with an inorganic acid or with a Lewis acid - preferably aluminium(III) chloride - dissolved in an inert solvent - preferably in a halogenated hydrocarbon and most preferably in dichloromethane - and the cyclization product of type 41 resulting from this reaction is isolated

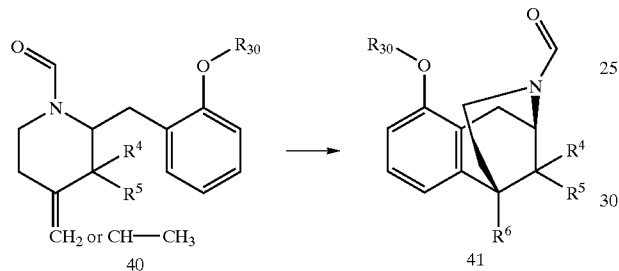

and i) the benzomorphan derivative resulting from the cyclization reaction is dissolved in a polar solvent - preferably in a $C_1$–$C_4$-alkanol, most preferably in n-propanol - and reacted with an acidically reacting compound - preferably with the aqueous solution of an inorganic acid and most preferably with concentrated hydrochloric acid - and the deformylated norbenzomorphan of type 42 resulting from this reaction is optionally isolated in the form of its acid addition salt

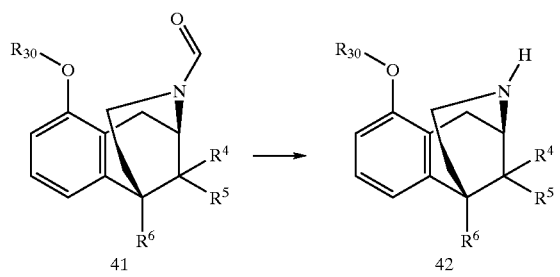

and j) if the stereoisomers have not yet been separated, at this stage the stereoisomers are separated in a manner known per se and after the release of the free benzomorphan base the phenolether is cleaved with an acidically reacting compound - preferably with an inorganic acid and most preferably with hydrobromic acid - and the cleavage product of type 43 is isolated k) the cleavage product 43 is reacted with a compound of type Z—$CHR_8$—R' wherein Z denotes a secondary amino substituted leaving group preferably a halogen such as chlorine, bromine, iodine or an organic sulfonate, preferably trifluoromethanesulfonate - and R' denotes —$CR^1R^2XR^7$,

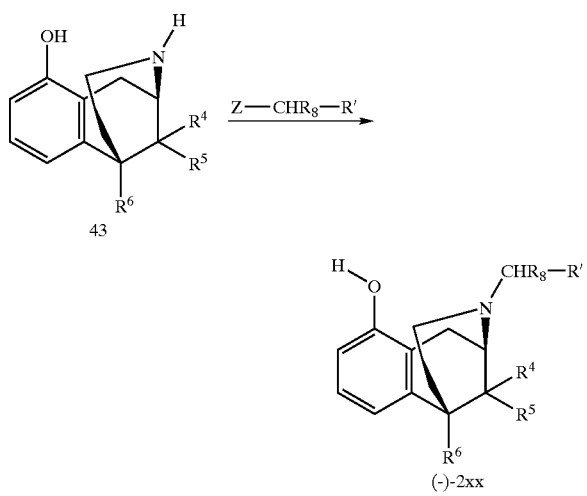

or is reacted with a compound of type YC(O)R' wherein Y denotes a secondary amino nitrogen substituted leaving group, preferably a halogen such as chlorine, bromine, iodine or an organic sulfonate, preferably trifluoromethanesulfonate - and R' denotes —$CR^1R^2XR^7$, and subsequently the carbonyl compound is reduced to the compound (−)-2xx as shown above

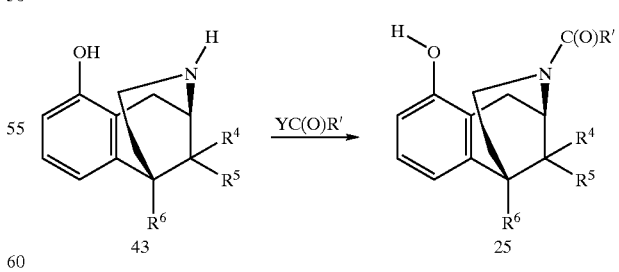

or reacted with an aldehyde of general formula HC(O)—R', wherein R' denotes - $CR^1Rp^2XR^7$, and the resulting Schiff base 26 is reduced to the compound (−)-22xx as shown above

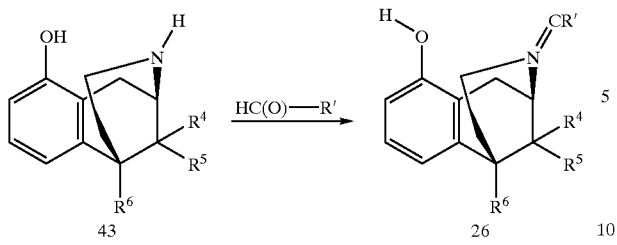

and l) optionally within the framework of an electrophilic substitution the substituent $R^3$ is introduced

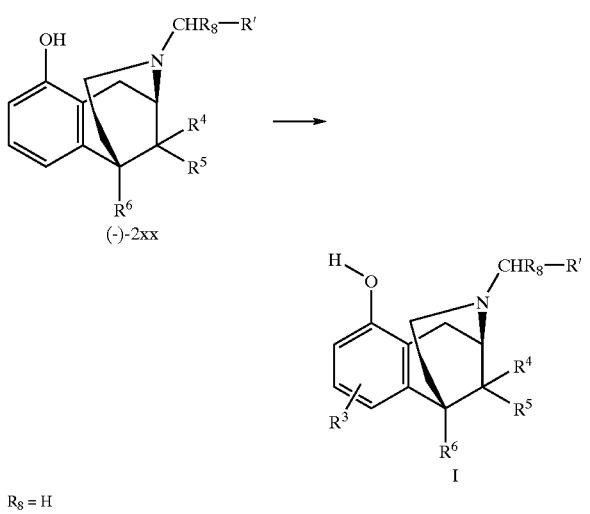

$R_8 = H$

Various other embodiments of the processes will be apparent to the skilled person from the present description. However, it is expressly pointed out that these Examples and the associated description are provided solely for the purpose of illustration and are not to be regarded as restricting the invention.

In addition, reference is expressly made to the contents of German Patent Application No. 197 40 110.4, from which the present application claims priority.

EXAMPLES

Example 1

Ethyl 3-amino-4-(2-methoxyphenyl)-2-methylbutanoate 13

150 g of zinc in 1.5 L of absolute dichloromethane are combined with 15 mL of trimethylchlorosilane under nitrogen and stirred for 30 minutes at ambient temperature. Then 900 mL of absolute tetrahydrofuran (THF) are added and heated to 42° C. To this is added dropwise a mixture of 147 g (1.0 mol) of 2-methoxybenzylcyanide 11 and 362 g (2,0 mol) of ethyl 2-bromopropionate in 100 mL of THF and the resulting mixture is then refluxed for a further 2 h. It is left to cool, decanted off from the excess zinc and after cooling to about 5° C. combined with 70 g (1.8 mol) of sodium borohydride. Then 250 mL of ethanol are added dropwise (development of gas). The mixture is left to react for 3 h at 5° C., 1 liter of 2 N hydrochloric acid is slowly added, the phases are separated and the aqueous phase is extracted twice with 200 mL of dichloromethane. The solvent of the combined organic phase is eliminated in vacuo, the residue is combined with ice and toluene and made alkaline with conc. ammonia. The phases are separated and the aqueous phase is extracted twice more with 800 mL of toluene. The combined organic phases are dried over magnesium sulfate, and the solvent is eliminated in vacuo. Yield 149 g (61%) oil.

Example 2

Ethyl 3-(2-ethoxycarbonylethyl)amino-4-(2-methoxyphenyl)-2-methylbutanoate 14

148 g (0.6 mol) of ethyl 3-amino-4-(2-methoxyphenyl)-2-methylbutanoate 13 and 119 g (1.2 mol) of ethyl acrylate are dissolved in 250 mL of abs. ethanol and refluxed for 6 h. Then the mixture is concentrated by evaporation in vacuo. The residue is again taken up in 300 mL of toluene and once more concentrated by evaporation in vacuo. 210 g (100%) of the desired product are isolated as an oil.

Example 3

2-(2-methoxyphenyl)methyl-3-methyl-4-piperidone 15

210 g (0.6 mol) of ethyl 3-(2-ethoxycarbonylethyl)-amino-4-(2-methoxyphenyl)-2-methylbutanoate 14 are dissolved in 3 1 toluene and first about 100 mL of a solvent/water mixture are entrained. The mixture is cooled to about 70° C., combined with 80 g (0.7 mol) of potassium tert-butoxide and heated for 30 minutes to 105° C., while the ethanol formed is distilled off. Then the mixture is left to cool and the solvent is eliminated in vacuo. The residue is combined with 400 mL of ethanol and 200 mL of 40% sodium hydroxide solution and refluxed for 3 h. The alcohol is eliminated in vacuo and the aqueous phase is extracted three times with 400 mL of diethylether (ether). The combined organic phases are dried over magnesium sulfate, and the solvent is eliminated in vacuo. Yield 109 g (78%) oil.

Example 4

(+)-4-ethylen-2-(2-methoxyphenyl)methyl-3,3-dimethylpiperidine (+)-7

74.2 g (200 mmol) of ethyl-triphenylphosphonium bromide are suspended in 200 mL of absolute tetrahydrofuran and combined under nitrogen with 80 mL of a 2.5 N solution of n-butyllithium in hexane. The mixture is stirred for 30 min at 30° C., and then combined with a solution of 23 g (93 mmol) of the piperidone (+)-6 in 100 mL of THF. This is then left to react for 12 h at ambient temperature, 100 mL of water are added and the THF is eliminated in vacuo. The residue is extracted three times with 200 mL of ethyl acetate and the combined organic extracts are washed again with 50 mL of water, dried over magnesium sulfate and the solvent is eliminated in vacuo. The residue is purified over a flash column (300 mL of silica gel; 41 cyclohexane/ethyl acetate 3:1). The desired product is isolated as an oil in a yield of 17.4 g (72%).

The following was prepared analogously to Example 4:

2-(2-methoxyphenyl)methyl-3-methyl-4-methylene-piperidine 16

20.1 g (56 mmol) of methyl-triphenylphosphonium bromide, 6.3 g (56 mmol) of potassium tert-butoxide and 11 g (47 mmol) of 2-(2-methoxyphenyl)methyl-3-methyl-4-piperidone 15 in 200 mL of abs. THF are used. The product is crystallized from acetone as the oxalate. Yield: 13.1 g (87%); melting point: 145° C.

Example 5

(+)-4-ethylene-N-formyl-2-(2-methoxyphenyl)
methyl-3,3-dimethyl-piperidine (+)-8

3.5 g (12.6 mmol) of (+)-4-ethylene-2-(2-methoxyphenyl) methyl-3,3-dimethyl-piperidine 7 are stirred with 20 mL of n-butylformate for 4 h at 80° C. The mixture is then evaporated down in vacuo. 3.6 g (100%) of the desired product are left in the form of an oil.

The following was prepared analogously to Example 5:

N-formyl-2-(2-methoxyphenyl)methyl-3-methyl-4-methylene-piperidine 17

8 g (34 mmol) of 2-(2-methoxyphenyl)methyl-3-methyl-4-methylene-piperidine 16 as base and 30 mL of n-butylformate were used. Yield: 9.1 g (100%) as an oil.

Example 6

N-benzyl-2-(2-methoxyphenyl)methyl-4-methyl-piperi-3-dene 22

6.0 g (250 mmol) of magnesium chips and some iodine are placed in 150 mL of ether. To this are added dropwise 31.32 g (200 mmol) of 2-methoxybenzyl chloride in 50 mL of ether so that the mixture boils gently. It is left to react for 1 h. The Grignard reagent thus obtained is then rapidly added dropwise to a suspension of 52.8 g (200 mmol) of N-benzyl-4-methyl-pyridinium bromide in 100 mL of ether cooled to −10° C. under nitrogen. The mixture is left to react for 2.5 h. Then the entire reaction mixture is added to 200 mL of a 10% ammonium chloride solution. The organic phase is separated off and the aqueous phase is extracted twice more with 100 mL of ether. The combined organic phases are dried over magnesium sulfate and the solvent is eliminated in vacuo. To avoid oxidation, the rotary evaporator is ventilated with nitrogen. The residue is immediately dissolved in 250 mL of methanol and 9.5 g (250 mmol) of sodium borohydride and 20 mL of 2 N sodium hydroxide solution are added. The mixture is stirred overnight at room temperature (RT) and evaporated down in vacuo. The aqueous residue is extracted twice with 150 mL of ether and the combined organic phase is concentrated by evaporation in vacuo. The residue is taken up in ethyl acetate and extracted five times with 150 mL of 2 N hydrochloric acid. The combined aqueous phase is then made alkaline again with sodium hydroxide solution and extracted twice with 200 mL of ethyl acetate. The combined organic phases are dried over magnesium sulfate (MgSO$_4$) and the solvent is eliminated in vacuo. The residue is purified by filtration over 200 mL of silica gel (eluant: ether). 31 g (51%) of the desired product are obtained as an oil.

Example 7

(−)-5-Ethyl-2-formyl-4'-methoxy-9,9-dimethyl-6,7-benzomorphan (−)-9

3.6 g (12.6 mmol) of (+)-4-ethylene-N-formyl-2-(2-methoxyphenyl)methyl-3,3-dimethyl-piperidine 8 are combined with 35 mL of methanesulfonic acid and stirred for 3 h at 80° C. The reaction mixture is cooled and poured onto 50 g ice, neutralized with ammonia and extracted twice with 100 mL of ethyl acetate. The combined organic extracts are washed again with 50 mL of water, dried over MgSO$_4$ and the solvent is eliminated in vacuo. The residue is purified over a flash column (50 mL of silica gel; 750 mL of cyclohexane/ethyl acetate 3:1). The desired product is isolated as an oil in a yield of 2.1 g (58%).

The following are prepared analogously to Example 7:

N-formyl-4'-methoxy-5,9-dimethyl-6,7-benzomorphan 18

5.0 g (19 mmol) of N-formyl-2-(2-methoxyphenyl)-methyl-3-methyl-4-methylene-piperidine 17 and 30 mL of methanesulfonic acid are used. 4.8 g (96%) of the desired product (oil) are obtained as a mixture of 90% α-epimer and 10% β-epimer.

N-benzyl-4'-methoxy-9-methyl-6,7-benzomorphan-oxalate 23OX 31 g (100 mmol) of N-benzyl-2-(2-methoxyphenyl) methyl-4-methyl-piperi-3-dene 22 and 100 mL of methane-sulfonic acid are used. The residue is dissolved in 100 mL of methanol and briefly boiled with 60 g activated charcoal and suction filtered while hot over silica gel. The solvent is eliminated in vacuo, the residue is dissolved in ether and the oxalate is precipitated with oxalic acid. 30 g (75%) are obtained; melting point: 152° C. (MK 1–11).

Example 8

4'-methoxy-9-methyl-6,7-benzomorphan-oxalate 24OX 30 g (75 mmol) of N-benzyl-4'-methoxy-9-methyl-6,7-benzomorphan-oxalate (23OX) are dissolved in 600 mL of methanol and hydrogenated at 60° C. and 5 bar on 3 g Pd/charcoal (10%). The mixture is cooled to 5° C. and the precipitated product is suction filtered. 17 g (56%) are obtained, melting point: 250° C. (MK 1–15).

Example 9

(−)-5-ethyl-4'-methoxy-9,9-dimethyl-6,7-benzomorphan (−)-10

2.0 g (6.9 mmol) of (−)-5-ethyl-2-formyl-4'-methoxy-9, 9-dimethyl-6,7-benzomorphan 9 are dissolved in 30 mL of n-propanol and heated with 10 mL of conc. hydrochloric acid in the microwave at 300 Watt for 2h. Then the solvent is eliminated in vacuo, the residue is combined with 15 mL of ice water and extracted twice with 20 mL of ethyl acetate (which is discarded). The aqueous phase is neutralized with conc. ammonia and extracted three times with 20 mL of ethyl acetate. The combined organic extracts are dried over MgSO$_4$ and the solvent is eliminated in vacuo. The residue is dissolved in acetone and the hydrochloride is precipitated with ethereal hydrochloric acid. Yield: 1.7 g (82%), melting point:

>250° C., $[\alpha]_D^{25}$=(−) 43.0° (c=1 in methanol).

The following is prepared analogously to Example 9:

4'-methoxy-5,9-dimethyl-6,7-benzomorphan 19

4.8 g (18 mmol) of N-formyl-4'-methoxy-5,9-dimethyl-6,7-benzomorphan 18, 50 mL of n-propanol and 50 mL of conc. hydrochloric acid are used. The mixture is refluxed for 8 h. Yield: 2.9 g (57%). A sample is converted with oxalic acid into the corresponding oxalate (HB), which has a melting point of 229° C.

Example 10

(−)-(1R,9α)-4'-methoxy-5,9-dimethyl-6,7-benzomorphan (−)-19

9.5 g (41 mmol) of 4'-methoxy-5,9-dimethyl-6,7-benzomorphan 19 are dissolved in 80 mL of ethanol and combined with 6.2 g (41 mmol) of R-(+)-tartaric acid. The crystals precipitated are suction filtered and recrystallized from methanol twice. Yield 2.6 g (17%), melting point: 236° C., ee>98% (determined by NMR-spectroscopy using the free base by the addition of shift reagent). The tartrate is dissolved in water, the base is liberated with potassium carbonate and extracted twice with 50 mL of ethyl acetate. The combined organic extracts are dried over MgSO$_4$ and the solvent is eliminated in vacuo. 1.6 g of the free base are obtained.

Example 11

(−)-(1R,9α)-4'-hydroxy-5,9-dimethyl-6,7-benzomorphan-hydrobromide (−)-4aBr 1.5 g (6.5 mmol) of (−)-4'-methoxy-5,9-dimethyl-6,7-benzomorphan (−)-19 are refluxed with 15 mL of 48% hydrobromic acid for 2 h. Then the mixture is concentrated by evaporation in vacuo and the residue is digested with THF. 1.5 g (78%) of the desired product are obtained as the hydrobromide (amorphous precipitate).

The following is prepared analogously to Example 11:

4'-hydroxy-9-methyl-6,7-benzomorphan-oxalate-hydrobromide 5aBr 9.5 g (31 mmol) of 4'-methoxy-9-methyl-6,7-benzomorphan-oxalate 24OX are first dissolved in a little water and converted into the free base with 7 g potassium carbonate. The mixture is extracted three times with 200 mL of ethyl acetate and the solvent is eliminated from the combined organic phase. Then 30 mL of 48% hydrobromic acid are added. 6.1 g (70%) of the desired hydrobromide is obtained; melting point: 227° C.

Example 12

(−)-(1R,9α,2"S)-2-(2"-benzyloxy)propyl-4'-hydroxy-5,9-dimethyl-6,7-benzomorphan-hydrochloride (−)-4bCl 0.75 g (2.5 mmol) of (−)-4'-hydroxy-5,9-dimethyl-6,7-benzomorphan-hydrobromide (−)-4aBr are suspended in 15 mL of dichloromethane and combined with 3 mL of N-methylmorpholine. After 30 minutes the mixture is cooled to −5° C. and a solution of 1.1 g (5.5 mmol) of (−)-S-2-benzyloxypropionic acid chloride in 10 mL of dichloromethane is slowly added dropwise. The mixture is stirred for a further 30 minutes at −5° C., combined with 20 mL of 2 N hydrochloric acid and the organic phase is separated off. The organic phase is dried over MgSO$_4$, the solvent is eliminated in vacuo and the residue is taken up in 40 mL of THF. To this solution are added 0.5 g (13 mmol) of LiAlH$_4$ whereupon the temperature rises to 35 ° C. The mixture is left to react for 30 min, then 0.4 mL of water and 0.2 mL of 5 N sodium hydroxide solution are added and the inorganic precipitate is separated off. The precipitate is washed with 100 mL of THF and the combined organic phases are concentrated by evaporation in vacuo. The residue is taken up in 100 mL of ether, dried over MgSO4 and the hydrochloride is precipitated with ethereal hydrochloric acid. The crystals are separated off and washed with acetone. Yield: 0.6 g (55%), melting point: 227° C., $[\alpha]_D^{25}$=(−) 13.3° (c=1 in methanol).

The following are prepared analogously to Example 12:

(−)-(1R,9α,2"R)-2-(2"-benzyloxy)propyl-4'-hydroxy-5,9-dimethyl-6,7-benzomorphan-hydrochloride (−)-4c Cl 0.75 g (2.5 mmol) of (−)-4'-hydroxy-5,9-dimethyl-6,7-benzomorphan-hydrobromide (−)-4aBr and 1.1 g (5.5 mmol) of (+)-R-2-benzyloxypropionic acid chloride are used. Yield: 0.7 g (65%), melting point: 217° C., $[\alpha]_D^{25}$=(−) 76.1° (c=1 in methanol).

(−)-(1R,9α)- 4'-hydroxy-5,9-dimethyl-2-[2-(2-phenoxy)ethoxy]ethyl -6,7-benzomorphan-hydrochloride (−)-4cCl 0.75 g (2.5 mmol) of (−)-4'-hydroxy-5,9-dimethyl-6,7-benzomorphan-hydrobromide (−)-4aBr and 1.1 g (5.5 mmol) of phenoxyethoxyacetylchloride are used. Yield: 0.2 g (20%) amorphous powder.

(−)-(1R,2"S)-2-(2"-benzyloxy)propyl-4'-hydroxy-5,9,9-trimethyl-6,7-benzomorphan-hydrochloride (−)-2bCl 1.6 g (6.9 mmol) of (−)-4'-hydroxy-5,9,9-trimethyl-6,7-benzomorphan (−)-2a and 2,3 g (11.6 mmol) of (−)-S-2-benzyloxypropionic acid chloride are used. Yield: 2.1 g (73%), melting point: 254° C., $[\alpha]_D^{25}$=(−) 20.7° (c=1 in methanol).

(+)-(1S,2"R)-2-(2"-benzyloxy)propyl-4'-hydroxy-5,9,9-trimethyl-6,7-benzomorphan-hydrochloride (+)-2bCl 1.5 g (6.5 mmol) of (+)-4'-hydroxy-5,9,9-trimethyl-6,7-benzomorphan (+)-2a and 1.5 g (7.6 mmol) of (+)-R-2-benzyloxypropionic acid chloride are used. Yield: 1.4 g (52%), melting point: 256° C., $[\alpha]_D^{25}$=(+) 20.3° (c=1 in methanol).

(−)-(1R,2"R)-2-(2"-benzyloxy)propyl-4'-hydroxy-5,9,9-trimethyl-6,7-benzomorphan-hydrochloride (−)-2cCl 1.6 g (6.9 mmol) of (−)-4'-hydroxy-5,9,9-trimethyl-6,7-benzomorphan (−)-2a and 1.5 g (7.6 mmol) of (+)-R-2-benzyloxypropionic acid chloride are used. Yield: 1.7 g (59%), melting point: 245° C., $[\alpha]_D^{25}$=(−) 96.5° (c=1 in methanol).

(+)-(1S,2"S)-2-(2"-benzyloxy)propyl-4'-hydroxy-5,9,9-trimethyl-6,7-benzomorphan-hydrochloride (+)-2cCl 1.6 g (6.9 mmol) of (+)-4'-hydroxy-5,9,9-trimethyl-6,7-benzomorphan (+)-2a and 2,3 g (11.6 mmol) of (−)-S-2-benzyloxypropionic acid chloride are used. Yield: 2.0 g (70%), melting point: 245° C., $[\alpha]_D^{25}$=(+) 97.8° (c=1 in methanol).

(−)-(1R,2"S)-2-(2"-(2'"-fluorobenzyl)oxy)propyl-4'-hydroxy-5,9,9-trimethyl-6,7-benzomorphan-hydrochloride ((−)-2dCl)

0.8 g (3.4 mmol) of (−)-4'-hydroxy-5,9,9-trimethyl-6,7-benzomorphan (−)-2a and 1.4 g (6.5 mmol) of (−)-S-2-(2'-fluorobenzyl)oxypropionic acid chloride are used. Yield: 0.9 g (61%), melting point: 212° C., $[\alpha]_D^{25}$=(−) 24.7° (c=1 in methanol).

(−)-(1R,2"R)-2-(2"-(2'"-fluorobenzyl)oxy)propyl-4'-hydroxy-5,9,9-trimethyl-6,7-benzomorphan-hydrochloride (−)-2eCl 0.5 g (2,3 mmol) of (−)-4'-hydroxy-5,9,9-trimethyl-6,7-benzomorphan (−)-2a and 0.6 g (3.0 mmol) of (+)-R-2-(2'-fluorobenzyl)oxypropionic acid chloride are used. Yield: 0.7 g (70%), melting point: 145° C., $[\alpha]_D^{25}$=(−) 88.4° (c=1 in methanol).

(−)-(1R,2"S)-2-(2"-(4'"-fluorobenzyl)oxy)propyl-4'-hydroxy-5,9,9-trimethyl-6,7-benzomorphan-hydrochloride (−)-2fCl 0.8 g (3.4 mmol) of (−)-4'-hydroxy-5,9,9-trimethyl-6,7-benzomorphan (−)-2a and 1.4 g (6.5 mmol) of (−)-S-2-(2'-fluorobenzyl)oxypropionic acid chloride are used. Yield: 1.0 g (68%), melting point: 250° C., $[\alpha]_D^{25}$=(−) 21.9° (c=1 in methanol).

(−)-(1R,2"R)-2-(2"-(4'"-fluorobenzyl)oxy)propyl-4'-hydroxy-5,9,9-trimethyl-6,7-benzomorphan-hydrochloride (−)-2gCl 0.5 g (2,3 mmol) of (−)-4'-hydroxy-5,9,9-trimethyl-6,7-benzomorphan (−)-2a and 0.6 g (3.0 mmol) of (+)-R-2-(2'- fluorobenzyl)oxypropionic acid chloride are used. Yield: 0.6 g (58%), melting point: 128° C., $[\alpha]_D^{25}=(-)$ 95.4° (c=1 in methanol).

(−)-(1R,2"S)-2-(2"-(2'",6'"-difluorobenzyl)oxy)-propyl-4'-hydroxy-5,9,9-trimethyl-6,7-benzomorphan-hydrochloride (−)-2hCl 1.5 g (6.5 mmol) of (−)-4'-hydroxy-5,9,9-trimethyl-6,7-benzomorphan (−)-2a and 2.4 g (10.2 mmol) of (−)-S-2-(2',6'-difluorobenzyl)oxypropionic acid chloride are used. Yield: 2.0 g (68%), melting point: 245° C. $[\alpha]_D^{25}=(-)$ 272.3° (c=1 in methanol).

(−)-(1R,2"S)-2-(2"-(2'",6'"-dichlorobenzyl)oxy)propyl-4'-hydroxy-5,9,9-trimethyl-6,7-benzomorphan-hydrochloride (−)-2iCl 2.3 g (10 mmol) of (−)-4'-hydroxy-5,9,9-trimethyl-6,7-benzomorphan (−)-2a and 3.2 g (12 mmol) of (−)-S-2-(2',6'-dichlorbenzyl)oxypropionic acid chloride are used. Yield: 2.8 g (58%), melting point: 260° C., $[\alpha]_D^{25}=(-)$ 14.10° (c=1 in methanol).

(−)-(1R,2"S)-2-(2"-(2'"-methyl-benzyl)oxy)propyl-4'-hydroxy-5,9,9-trimethyl-6,7-benzomorphan-hydrochloride (−)-2jCl 0.8 g (3.4 mmol) of (−)-4'-hydroxy-5,9,9-trimethyl-6,7-benzomorphan (−)-2a and 1.4 g (6.5 mmol) of (−)-S-2-(2'-methyl-benzyl)oxypropionic acid chloride are used. Yield: 0.8 g (55%), melting point: 249° C., $[\alpha]_D^{25}=(-)$ 10.9° (c=1 in methanol).

(−)-(1R,2"S)-2-(2"-cyclohexylmethoxy)propyl-4'-hydroxy-5,9,9-trimethyl-6,7-benzomorphan-hydrochloride (−)-2kCl 1.9 g (8.2 mmol) of (−)-4'-hydroxy-5,9,9-trimethyl-6,7-benzomorphan (−)-2a and 2.0 g (10 mmol) of (−)-S-2-(2'-cyclohexylmethoxy)propionic acid chloride are used. Yield: 1.8 g (52%), melting point: 249° C., $[\alpha]_D^{25}=(-)$ 24.6° (c=1 in methanol).

(−)-(1R,2"R)-2-(2"-cyclohexylmethoxy)propyl-4'-hydroxy-5,9,9-trimethyl-6,7-benzomorphan-hydrochloride (−)-2lCl 1.9 g (8.2 mmol) of (−)-4'-hydroxy-5,9,9-trimethyl-6,7-benzomorphan (−)-2a and 2.0 g (10 mmol) of (+)-R-2-(2'-cyclohexylmethoxy)propionic acid chloride are used. Yield: 1.7 g (49%), melting point: 140° C., $[\alpha]_D^{25}=(-)$ 92.2° (c=1 in methanol).

(−)-(1R)-4'-hydroxy-2-(5"-phenoxy)pentyl-5,9,9-trimethyl-6,7-benzomorphan-hydrochloride ((−)-2mCl)

3.0 g (13 mmol) of (−)-4'-hydroxy-5,9,9-trimethyl-6,7-benzomorphan (−)-2a and 3.2 g (15 mmol) of 5-phenoxypentanoic acid chloride are used. Yield: 2.4 g (44%), melting point: 149° C., $[\alpha]_D^{25}=(-)$ 74.6° (c=1 in methanol).

(−)-(1R)-4'-hydroxy-2-(2"-(2'"-phenyl)ethoxy)ethyl-5,9,9-trimethyl-6,7-benzomorphan-hydrochloride (−)-2nCl 2.0 g (8.7 mmol) of (−)-4'-hydroxy-5,9,9-trimethyl-6,7-benzomorphan (−)-2a and 2.2 g (11 mmol) of 2-phenylethoxyacetic acid chloride are used. Yield: 1.7 g (48%), melting point: 204° C., $[\alpha]_D^{25}=(-)$ 72.4° (c=1 in methanol).

(−)-(1R)-4'-hydroxy-2-(4"-phenoxy)butyl-5,9,9-trimethyl-6,7-benzomorphan-hydrochloride (−)-2oCl 1.0 g (4.3 mmol) of (−)-4'-hydroxy-5,9,9-trimethyl-6,7-benzomorphan (−)-2a and 1.2 g (6 mmol) of 4-phenoxybutyric acid chloride are used. Yield: 0.7 g (39%), melting point: 250° C., $[\alpha]_D^{25}=(-)$ 82.8° (c=1 in methanol).

(−)-(1R)-2-(2"-benzyloxy)ethyl-4'-hydroxy-5,9,9-trimethyl-6,7-benzomorphan-hydrochloride (−)-2pCl 2.3 g (10 mmol) of (−)-4'-hydroxy-5,9,9-trimethyl-6,7-benzomorphan (−)-2a and 4.3 g (22 mmol) of 2-benzyloxyacetyl chloride are used. Yield: 2.5 g (62%), melting point: 253° C., $[\alpha]_D^{25}=(-)$ 78.1° (c=1 in methanol).

(−)-(1R)-2-(2"-(2'",6'"-difluorobenzyloxy)ethyl-4'-hydroxy-5,9,9-trimethyl-6,7-benzomorphan-hydrochloride (−)-2qCl 1.2 g (5 mmol) of (−)-4'-hydroxy-5,9,9-trimethyl-6,7-benzomorphan (−)-2a and 1.1 g (5 mmol) of 2-(2',6'-difluorobenzyloxyacetyl chloride are used. Yield: 1.5 g (68%), melting point: 246° C., $[\alpha]_D^{25}=(-)$ 71.0° (c=1 in methanol).

(−)-(1R)-2-(3"-(2'",6'"-difluorophenyl)propyl)-4'-hydroxy-5,9,9-trimethyl-6,7-benzomorphan-hydrochloride (−)-2rCl 1.9 g (8.2 mmol) of (−)-4'-hydroxy-5,9,9-trimethyl-6,7-benzomorphan (−)-2a and 1.7 g (8.3 mmol) of 3-(2',6'-difluorophenylpropionic acid chloride are used. Yield: 1.6 g (46%), melting point: >250° C., $[\alpha]_D^{25}=(-)$ 68.6° (c=1 in methanol).

Example 13

(+)-(1R,2"S)-2-(2"-benzyloxy)propyl-4'-hydroxy-5-methyl-6,7-benzomorphan-hydrochloride (+)-5bCl and (+)-(1S,2"S)-2-(2"-benzyloxy)propyl-4'-hydroxy-5-methyl-6,7-benzomorphan-hydrochloride (+)-5cCl 5.1 g (17 mmol) of 4'-hydroxy-9-methyl-6,7-benzomorphan-oxalate-hydrobromide 5aBr and 1.7 g (17 mmol) of N-methylmorpholine are dissolved in 20 mL of DMF and cooled to −5° C. A solution of 3.5 g (19 mmol) of (−)-S-2-benzyloxypropionic acid, 1.8 g (19 mmol) of methyl chloroformate and 2.0 g (19 mmol) of N-methylmorpholine in 20 mL of dichloromethane prepared at −5° C. is slowly added dropwise thereto. The mixture is left to react for 1 h at ambient temperature, the solvent is largely eliminated in vacuo, the residue is taken up in 60 mL of dichloromethane, extracted twice with 20 mL of 2 N hydrochloric acid and once with 20 mL of water. The organic phase is dried over $MgSO_4$ and the solvent is eliminated in vacuo. After the addition of a little ether the product crystallizes out (melting point: 110° C.), is suction filtered and taken up in 80 mL of THF. To this solution are added 0.8 g (21 mmol) of $LiAlH_4$, whereupon the temperature rises to 35° C. The mixture is left to react for 1 h, combined with 25 mL of water and 25 mL of 40% sodium tartrate solution. The organic phase is separated off, the aqueous phase is extracted twice with 100 mL of ether and the combined organic phases are concentrated by evaporation in vacuo. The residue is taken up in 100 mL of ether, dried over magnesium sulfate and the hydrochloride is precipitated with ethereal hydrochloric acid. The crystals are separated off and recrystallized from i-propanol. 1.1 g (17%) of (+)-5bCl are obtained, melting point: 246° C., $[\alpha]_D^{25}=(+)$ 11.8° (c=1 in methanol). The mother liquor was concentrated by evaporation, the base was liberated and chromatographed (300 g silica gel; ethyl acetate/cyclohexane 1:3). The hydrochloride is again precipitated with ethereal hydrochloric acid. 0.3 g (5%) of (+)-5cCl are obtained, melting point: 241° C., $[\alpha]_D^{25}=(+)$ 52.4° (c=1 in methanol).

The following are prepared analogously to Example 13:

(+)-(1R,2"S)-2-[2"-(2'",6'"-difluorobenzyloxy)]-propyl-4'-hydroxy-5-methyl-6,7-benzomorphan-hydrochloride (+)-5dCl and (+)-(1S,2"S)-2-(2"-(2'",6'"-difluorobenzyloxy))propyl-4'-hydroxy-5-methyl-6,7-benzomorphan-hydrochloride (+)-5eCl 4.0 g (14 mmol) of 4'-hydroxy-5-methyl-6,7-benzomorphan-hydrobromide 5aBr and 3.0 g (14 mmol) of (+)-R-2-(2',6'-difluorobenzyloxy)propionic acid are used. 0.3 g (5%) of (+)-5dCl are obtained, melting point: 122° C., $[\alpha]_D^{25}$=(+) 20.9° (c=1 in methanol) and 1.8 g (30%) of a mixture of (+)-5dCl and (+)-5eCl, melting point: 194° C., $[\alpha]_D^{25}$=(+) 42.2° (c=1 in methanol).

Example 14

(−)-(1R)-4'-hydroxy-5,9,9-trimethyl-2-[2"-(2'"-phenoxy)ethoxy]ethyl-6,7-benzomorphan-hydrochloride (−)-2uCl 1.5 g (6.5 mmol) of (−)-4'-hydroxy-5,9,9-trimethyl-6,7-benzomorphan (−)-2a and 1.5 g (7.5 mmol) of 2-(2-phenoxy)ethoxy-ethylchloride are dissolved in 20 mL of DMF, a catalytic quantity of KI and 1 g potassium carbonate are added. The mixture is stirred for 5 h at 130° C., and then the solvent is eliminated in vacuo. The residue is taken up in 100 mL of water, extracted three times with 100 mL of ethyl acetate and the combined organic extracts are once again washed with 50 mL of water, dried over MgSO$_4$ and the solvent is eliminated in vacuo. The residue is dissolved in 40 mL of ether and the hydrochloride is precipitated with ethereal hydrochloric acid. Yield: 1.4 g (50%), melting point: 190° C., $[\alpha]_D^{25}$=(−) 81.1° (c=1 in methanol).

The following are prepared analogously to Example 14:

(+)-(1S)-4'-hydroxy-5,9,9-trimethyl-2-[2"-(2'"-phenoxy)ethoxy]ethyl-6,7-benzomorphan-hydrochloride (+)-2vCl 1.5 g (6.5 mmol) of (+)-4'-hydroxy-5,9,9-trimethyl-6,7-benzomorphan (+)-2a and 1.5 g (7.5 mmol) of 2-(2-phenoxy)ethoxy-ethylchloride are used. Yield: 1.8 g (64%), melting point: 190° C., $[\alpha]_D^{25}$=(+) 81.0° (c=1 in methanol).

(−)-(1R,2"S)-2-[2"-(2'"-cyanobenzyl)oxy]propyl-4'-hydroxy-5,9,9-trimethyl-6,7-benzomorphan-hydrochloride (−)-2wCl 0.8 g (3.4 mmol) of (−)-4'-hydroxy-5,9,9-trimethyl-6,7-benzomorphan (−)-2a and 1.0 g (3.7 mmol) of 2-(2'-cyanobenzyl)oxypropyl S-methanesulfonate are used. Yield: 0.2 g (13%), melting point: 234° C.

(−)-(1R)-2-[2"-(2'"-cyclohexyloxy)ethoxy]ethyl-4'-hydroxy-5,9,9-trimethyl-6,7-benzomorphan-hydrochloride (−)-2xCl 1.0 g (4.3 mmol) of (−)-4'-hydroxy-5,9,9-trimethyl-6,7-benzomorphan (−)-2a and 1.1 g (5.4 mmol) of 2-(2'-cyclohexyloxy)ethoxy)ethylchloride are used. Yield: 0.7 g (37%), melting point: 204° C., $[\alpha]_D^{25}$=(−) 71.1° (c=1 in methanol).

(−)-(1R)-2-{2"-[2'"-(2,6-difluorophenoxy)ethoxy]-ethyl}-4'-hydroxy-5,9,9-trimethyl-6,7-benzomorphan-hydrochloride (−)-2yCl 2.3 g (10 mmol) of (−)-4'-hydroxy-5,9,9-trimethyl-6,7-benzomorphan (−)-2a and 2.8 g (12 mmol) of 2-(2'-(2,6-difluorophenoxy)ethoxy-ethylchloride are used. Yield: 2.3 g (49%), melting point: 183° C., $[\alpha]_D^{25}$=(−) 73.3° (c=1 in methanol).

(−)-(1R)-2-[2"-(2,6-difluorophenoxy)ethyl]-4'-hydroxy-5,9,9-trimethyl-6,7-benzomorphan-hydrochloride (−)-2zCl:

1.2 g (5 mmol) of (−)-4'-hydroxy-5,9,9-trimethyl-6,7-benzomorphan (−)-2a and 1.4 g (9.8 mmol) of 2-(2,6-difluorophenoxy)ethylchloride are used. Yield: 0.3 g (14%), melting point: 241° C.

(−)-(1R)-2-(2"-cyclohexyloxy)ethyl-4'-hydroxy-5,9,9-trimethyl-6,7-benzomorphan-hydrochloride (−)-2aaCl 1.2 g (5 mmol) of (−)-4'-hydroxy-5,9,9-trimethyl-6,7-benzomorphan (−)-2Oa and 1.1 g (6.8 mmol) of 2-cyclohexyloxy-ethyl chloride are used. Yield: 0.8 g (41%), melting point: >250° C., $[\alpha]_D^{25}$=(−) 71.1° (c=1 in methanol).

(−)-(1R)-2-[2"-(2'"-tert-butyloxy)ethoxy]ethyl-4'-hydroxy-5,9,9-trimethyl-6,7-benzomorphan-hydrochloride (−)-2acCl 1.5 g (6.4 mmol) of (−)-4'-hydroxy-5,9,9-trimethyl-6,7-benzomorphan (−)-2a and 1.4 g (7.7 mmol) of 2-(2'-tert-butyloxy)ethoxy)ethyl chloride are used. Yield: 0.8 g (30%), melting point: 209° C., $[\alpha]_D^{25}$=(−) 72.4° (c=1 in methanol).

Example 15

(−)-(1R)-5-ethyl-4'-hydroxy-9,9-dimethyl-2-(2-(2-phenoxy)ethoxy)ethyl-6,7-benzomorphan-hydrochloride 3bCl 1.0 g (3.4 mmol) of (−)-5-ethyl-4'-methoxy-9,9-dimethyl-6,7-benzomorphan (10) are refluxed with 20 mL of 48% hydrobromic acid for 2 h. Then the mixture is concentrated by evaporation in vacuo and the residue is dissolved twice with 20 mL of ethanol and evaporated down again. Then it is taken up in 20 mL of DMF and 800 mg (4.0 mmol) of 2-(2-phenoxy)ethoxy-ethyl chloride in 10 mL of DMF, a catalytic quantity of KI and 1 g of potassium carbonate are added. The mixture is stirred for 4 h at 80° C. the solvent is eliminated in vacuo. The residue is taken up in 100 mL of water, extracted three times with 100 mL of ethyl acetate and the combined organic extracts are again washed with 50 mL of water, dried over MgSO$_4$ and the solvent is eliminated in vacuo. The residue is dissolved in 40 mL of ether and the hydrochloride is precipitated with ethereal hydrochloric acid. Yield: 1.0 g (66%), melting point: 90° C. (decomposition).

Example 16

(−)-(1R)-4'-hydroxy-2-(2"-phenylethyl)-5,9,9-trimethyl-6,7-benzomorphan-hydrochloride (−)-2adCl 1.0 g (4.3 mmol) of (−)-4'-hydroxy-5,9,9-trimethyl-6,7-benzomorphan (−)-2a and 1.0 g (8.3 mmol) of phenylacetaldehyde are dissolved in 20 mL of methanol, combined with a molecular sieve and stirred for 3 h at RT. Then the molecular sieve is filtered off and the filtrate is combined with 0.6 g (9.5 mmol) of sodium cyanoborohydride and 1.2 mL of glacial acetic acid. The mixture is left to stand for about 12 hours, combined with 20 mL of 4 N hydrochloric acid and evaporated down in vacuo. The residue is mixed with a little acetone and the crystals are suction filtered. Yield: 0.9 g (56%), melting point: 250° C. $[\alpha]_D^{25}$=(−) 80.04° (c=1 in methanol).

The following is prepared analogously to Example 16:

(−)-(1R)-4'-hydroxy-2-(2"-phenylpropyl)-5,9,9-trimethyl-6,7-benzomorphan-hydrochloride (−)-2aeCl 1.0 g (4.3 mmol) of (−)-4'-hydroxy-5,9,9-trimethyl-6,7-benzomorphan (−)-2a, 1.2 g (8.9 mmol) of 3-phenylpropionaldehyde and 0.6 g (9.5 mmol) of sodium cyanoborohydride are used. Yield: 0.8 g (48%), melting point: >250° C., $[\alpha]_D^{25}$=(−) 75.1° (c=1 in methanol).

Example 17

(−)-(1R)-4'-hydroxy-2-[2"-(2'"-phenylamino)ethoxy]ethyl-5,9,9-trimethyl-6,7-benzomorphan-dihydrochloride (−)-2aeCl2

1.3 g (5.6 mmol) of (−)-4'-hydroxy-5,9,9-trimethyl-6,7-benzomorphan (−)-2a and 1.7 g (5.6 mmol) of 2-(N-phenyl- 2"-tert-butoxycarbonylamino)-ethoxyethyl chloride are dissolved in 50 mL of DMF, a catalytic quantity of KI and 1 g potassium carbonate are added. The mixture is stirred for 7 h at 110° C. and then the solvent is eliminated in vacuo. The residue is taken up in 100 mL of water, extracted three times with 100 mL of ethyl acetate and the combined organic extracts are once again washed with 50 mL of water, dried over $MgSO_4$ and the solvent is eliminated in vacuo. The residue is purified over a flash column (120 mL of silica gel; ethyl acetate/ cyclohexane 1:1) and stirred with 50 mL of conc. hydrochloric acid for 30 minutes at RT. Then the mixture is diluted with 150 mL of ice water, extracted once with 50 mL of ethyl acetate (discarding the organic phase), and made alkaline with conc. ammonia. It is extracted three times with 100 mL of ethyl acetate, the combined organic extracts are dried over $MgSO_4$ and the solvent is eliminated in vacuo. The residue is dissolved in 10 mL of ethanol and the hydrochloride is precipitated with ethereal hydrochloric acid. Yield: 0.7 g (27%), melting point: 112° C., $[\alpha]_D^{25}=(-)$ 75.8° (c=1 in methanol).

Example 18

(−)-(1R,2"S)-2-(2"-benzyloxy)propyl-3'-chloro-4'-hydroxy-5,9,9-trimethyl-6,7-benzomorphan-hydrochloride (−)-2agCl and (−)-(1R,2"S)-2-(2"-benzyloxy)propyl-1'-chloro-4'-hydroxy-5,9,9-trimethyl-6,7-benzomorphan-hydrochloride (−)-2ahCl 3 g (7.3 mmol) of (−)-(1R,2"S)-2-(2"-benzyloxy)propyl-4'-hydroxy-5,9,9-trimethyl-6,7-benzomorphan-hydrochloride (−)-2bCl and 1.0 g (7.3 mmol) of N-chlorosuccinimide are suspended in 70 mL of glacial acetic acid and stirred for 24 h at ambient temperature during which time the suspension goes into solution. Then the mixture is concentrated by evaporation in vacuo, the residue is combined with 100 mL of ice-cold 2 N sodium hydroxide solution and extracted three times with 100 mL of ethyl acetate. The combined organic phases are dried over $MgSO_4$ and the solvent is eliminated in vacuo. Then the residue is chromatographed on silica gel (180 g silica gel; cyclohexane/ethyl acetate 5:1). The suitable fractions are concentrated by evaporation and the residue is dissolved in 15 mL of acetone and the hydrochloride is precipitated with ethereal hydrochloric acid. 0.4 g (12%) of (−)-2agCl is obtained, melting point: 204° C., $[\alpha]_D^{25}=(-)$ 21.5° (c=1 in methanol) and 0.6 g (18%) of (−)-2ahCl is obtained, melting point: 258° C., $[\alpha]_D^{25}=(-)$ 4.6° (c=1 in methanol).

The following are some Examples of pharmaceutical preparations using the active substance:

Tablets:

| active substance of general formula I | 20 mg |
| magnesium stearate | 1 mg |
| lactose | 190 mg |

Solution for injection

| active substance of general formula I | 0.3 mg |
| sodium chloride | 0.8 g |
| benzalkonium chloride | 0.01 mg |
| water for injections | ad 100 mL |

A similar solution to that described above is suitable for nasal administration in a spray, or in conjunction with a device which produces an aerosol with a particle size preferably between 2 and 6 μM, for administration through the lungs.

Solution for infusion

A 5% by weight xylitol solution which contains the active substance in a concentration of 2 mg/mL, for example, is adjusted to a pH of about 4 with a sodium acetate buffer.

Infusion solutions of this kind may contain the active substance of general formula 1 in an amount of from 0.001 to 20% by weight, from 0.001 to 10 % by weight and most preferably from 0.0 1 to 5 % by weight, based on the total mass of the pharmaceutical preparation.

Capsules for inhalation

The active substance according to general formula I is packed into hard gelatine capsules in micronised form (particle size essentially between 2 and 6 μM), optionally with the addition of micronized carriers such as lactose. The preparation is inhaled using conventional devices for powder inhalation. Each capsule contains, e.g., between 0.2 and 20 mg of active substance and 0 to 40 mg of lactose.

Aerosol for inhalation

| active substance of general formula I | 1 part |
| soya lecithin | 0.2 parts |
| propellant gas mixture ad | 100 parts |

What is claimed is:

1. A compound of formula I

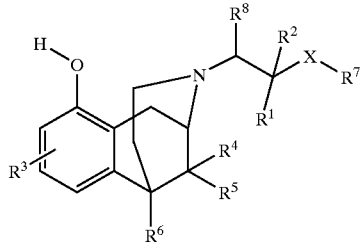

wherein:

X is a single bond, —O—, —O—CH₂—CH₂—NH—, or a branched or unbranched alkylene bridge having 1 to 8 carbon atoms and 0 to 2 oxygen atoms in the bridge;

$R^1$ is hydrogen, methyl, ethyl, or phenyl;

$R^2$ is hydrogen or methyl;

$R^3$ is hydrogen, fluorine, chlorine, bromine, hydroxy, methyl, or methoxy;

$R^4$ is hydrogen, methyl, or ethyl;

$R^5$ is hydrogen, methyl, or ethyl;

$R^6$ is hydrogen, methyl, or ethyl;

$R^7$ is tert-butyl, cyclohexyl, phenyl substituted with $R^9$ and $R^{10}$, which are identical or different, or

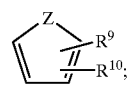

$R^8$ is hydrogen or $C_1$–$C_4$-alkyl;

Z is oxygen, NH, or sulfur;

$R^9$ is hydrogen, methyl, fluorine, chlorine, bromine, or methoxy;

$R^{10}$ is hydrogen, methyl, fluorine, chlorine, bromine, or methoxy;

an optical isomer thereof, a mixture of the enantiomers or a racemate thereof, a free base thereof, or an acid addition thereof with a pharmaceutically acceptable acid.

2. (−)-(1R,2″S)-2-(2″-Benzyloxy)propyl-4′-hydroxy-5,9,9-trimethyl-6,7-benzomorphan in the form of the free base or the corresponding acid addition salt with a pharmacologically acceptable acid.

3. (−)-(1R,2″S)-2-[2″-(2′″,6′″-Difluorobenzyl)-oxy]propyl-4′-hydroxy-5,9,9-trimethyl-6,7-benzomorphan in the form of the free base or the corresponding acid addition salt with a pharmacologically acceptable acid.

4. A pharmaceutical composition comprising a compound according to claim 1 and a pharmaceutically acceptable carrier.

5. The pharmaceutical composition according to claim 4, wherein the amount of the compound according to claim 1, based on the total mass of the pharmaceutical preparation, is in a range from 0.001 to 20% by weight.

6. The pharmaceutical composition according to claim 5, wherein the amount of the compound according to claim 1, based on the total mass of the pharmaceutical preparation, is in a range from 0.001 to 10% by weight.

7. The pharmaceutical composition according to claim 6, wherein the amount of the compound according to claim 1, based on the total mass of the pharmaceutical preparation, is in a range from 0.001 to 5% by weight.

8. A method for blocking the voltage-dependent sodium channel in a host suffering from a disease caused by dysfunction due to synaptic overstimulation, the method comprising administering to a host in need thereof the compound according to claim 1.

9. The method according to claim 8, wherein the disease caused by dysfunction due to synaptic overstimulation is selected from the group consisting of: hypoglycemia, hypoxia, anoxia, arrhythmia, spasms, cardiac ischemia, cardiac infarct, cardiac rhythm disorders, angina pectoris, and cerebral ischemia.

10. A method for blocking the voltage-dependent sodium channel in a host suffering from a neurodegenerative disorder, the method comprising administering to a host in need thereof the compound according to claim 1, in an amount effective to block the voltage-dependent sodium channel.

11. A method for blocking the voltage-dependent sodium channel in a host suffering from epilepsy, brain trauma, cerebral edema, cerebral stroke, perinatal asphyxia, amylotropic lateral sclerosis, Huntington's disease, Parkinson's disease, bipolar disorder, cyclophrenia, or hypotonia, comprising administering to a host in need thereof of a compound according to claim 19 in an amount effective to block the voltage-dependent sodium channel.

12. A method for the treatment or prophylaxis of pain, the method comprising administering to a host in need of such treatment or prophylaxis a therapeutically or prophylactically effective amount of the compound according to claim 1.

13. A method for anesthestizing a host, the method comprising administering to a host in need of such anesthesia an amount of the compound according to claim 1 sufficient to induce anesthesia in the host.

14. The compound of formula I according to claim 1, wherein:

X is O—$C_1$–$C_3$-alkylene or —O—$CH_2$—$CH_2$—O— or —O—$CH_2$—$CH_2$—NH— group;

$R^1$ is hydrogen, methyl, ethyl, or phenyl;

$R^2$ is hydrogen or methyl, $R^3$ is hydrogen, fluorine, chlorine, bromine, hydroxy, methyl, or methoxy;

$R^4$ is hydrogen, methyl, or ethyl;

$R^5$ is hydrogen, methyl, or ethyl;

$R^6$ is hydrogen, methyl, or ethyl;

$R^7$ is tert-butyl, cyclohexyl, phenyl optionally substituted by $R^9$ and $R^{10}$, which are identical or different, or

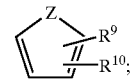

$R^8$ is hydrogen or $C_1$–$C_4$-alkyl;

Z is oxygen, NH, or sulfur;

$R^9$ is hydrogen, methyl, fluorine, chlorine, bromine, or methoxy;

$R^{10}$ is hydrogen, methyl, fluorine, chlorine, bromine, or methoxy;

an optical isomer thereof, a mixture of the enantiomers or a racemate thereof, a free base thereof, or an acid addition salt thereof with a pharmacologically acceptable acid.

15. The compound of formula I according to claim 1, wherein:

X is a single bond, —O—, $C_1$–$C_4$-alkylene, —O—$C_1$–$C_3$-alkylene, —O—$CH_2$–$CH_2$—O—, or —O—$CH_2$—$CH_2$—NH—;

$R^1$ is hydrogen, methyl, ethyl, or phenyl;

$R^2$ is hydrogen or methyl;

$R^3$ is hydrogen, fluorine, chlorine, bromine, hydroxy, methyl, or methoxy;

$R^4$ and $R^5$ is hydrogen or methyl, provided that at least one of $R^4$ and $R^5$ is methyl;

$R^6$ is hydrogen, methyl, or ethyl;

$R^7$ is tert-butyl, cyclohexyl, phenyl optionally substituted by $R^9$ and $R^{10}$, which are identical or different, or

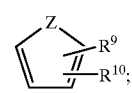

$R^8$ is hydrogen or $C_1$–$C_4$-alkyl;

Z is oxygen, NH, sulfur;

$R^9$ is hydrogen, methyl, fluorine, chlorine, bromine, or methoxy;

$R^{10}$ is hydrogen, methyl, fluorine, chlorine, bromine, or methoxy;

an optical isomer thereof, a mixture of the enantiomers or a racemate thereof, a free base thereof, or an acid addition salt thereof with a pharmacologically acceptable acid.

* * * * *